US012239382B2

(12) United States Patent
Hammudi et al.

(10) Patent No.: US 12,239,382 B2
(45) Date of Patent: *Mar. 4, 2025

(54) CONTROLLED TREATMENT OF TISSUE AND DYNAMIC INTERACTION WITH, AND COMPARISON OF, TISSUE AND/OR TREATMENT DATA

(71) Applicant: Gynesonics, Inc., Redwood City, CA (US)

(72) Inventors: Amer Hammudi, Tracy, CA (US); Jiayu Chen, Palo Alto, CA (US); Harry Kwan, San Francisco, CA (US); David Blair Toub, Wyncote, PA (US)

(73) Assignee: Gynesonics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,352

(22) Filed: Aug. 17, 2022

(65) Prior Publication Data
US 2023/0040427 A1    Feb. 9, 2023

Related U.S. Application Data

(63) Continuation of application No. 17/233,838, filed on Apr. 19, 2021, now Pat. No. 11,419,682, which is a (Continued)

(51) Int. Cl.
*A61B 8/12* (2006.01)
*A61B 8/08* (2006.01)
(Continued)

(52) U.S. Cl.
CPC ............... *A61B 34/10* (2016.02); *A61B 8/08* (2013.01); *A61B 8/12* (2013.01); *A61B 34/20* (2016.02);
(Continued)

(58) Field of Classification Search
CPC ............... G06F 11/3688; G06F 16/951; G06F 11/3684; G06F 13/102; G06F 13/4282;
(Continued)

(56) References Cited

U.S. PATENT DOCUMENTS 4,289,132 A    9/1981   Rieman
4,567,896 A    2/1986   Barnea et al.
(Continued)

FOREIGN PATENT DOCUMENTS

CN    1961841 A    5/2007
CN    2936129 Y    8/2007
(Continued)

OTHER PUBLICATIONS

U.S. Appl. No. 11/347,018 (U.S. Pat. No. 7,918,795), Method and Device for Uterine Fibroid Treatment, filed Feb. 2, 2006 (Apr. 5, 2011).
(Continued)

*Primary Examiner* — Rayeez R Chowdhury
(74) *Attorney, Agent, or Firm* — Knobbe, Martens, Olson & Bear, LLP

(57) ABSTRACT

An interactive treatment mapping and planning system enables a user to more quickly, thoroughly, and efficiently aggregate fibroid and/or treatment information from a user and/or one or more sets of databases, construct a fibroid map providing a visual representation of the aggregated fibroid information, generate information from the aggregated information about the fibroid to be treated and/or treatment procedure, develop a treatment plan based on the fibroid and/or treatment procedure information, provide real-time information gathered from treatment devices during the treatment procedure, and allow the user to interact with the treatment data.

17 Claims, 10 Drawing Sheets

Related U.S. Application Data continuation of application No. 16/408,790, filed on May 10, 2019, now Pat. No. 10,993,770, which is a continuation of application No. PCT/US2017/060674, filed on Nov. 8, 2017.

(60) Provisional application No. 62/421,119, filed on Nov. 11, 2016.

(51) Int. Cl.

| | | |
|---|---|---|
| *A61B 34/00* | (2016.01) | |
| *A61B 34/10* | (2016.01) | |
| *A61B 34/20* | (2016.01) | |
| *A61B 90/00* | (2016.01) | |
| *G06F 3/0484* | (2022.01) | |
| *G16H 40/63* | (2018.01) | |
| *A61B 5/00* | (2006.01) | |
| *A61B 17/00* | (2006.01) | |
| *A61B 17/42* | (2006.01) | |

(52) U.S. Cl.
CPC ............ *A61B 34/25* (2016.02); *A61B 90/37* (2016.02); *G06F 3/0484* (2013.01); *G16H 40/63* (2018.01); *A61B 5/4325* (2013.01); *A61B 2017/00053* (2013.01); *A61B 2017/4216* (2013.01); *A61B 2034/107* (2016.02); *A61B 2034/256* (2016.02); *A61B 2090/378* (2016.02); *A61B 2090/3975* (2016.02)

(58) Field of Classification Search
CPC .... G06F 15/17306; G06F 15/82; G06F 16/00; G06F 16/2246; G06F 16/2433; G06F 16/258; G06F 21/602; G06F 21/6218; G06F 21/6272; G06F 2119/14; G06F 2213/0002; G06F 3/017; G06F 30/20; G06F 9/546; G06F 1/163; G06F 1/1686; G06F 1/1694; G06F 1/26; G06F 11/1435; G06F 11/1441; G06F 3/011; G06F 18/2111; G06F 18/23; G06F 18/2411; G06F 18/24323; G06F 18/28; G06F 18/29; G06F 3/012; G06F 3/016
See application file for complete search history.

(56) References Cited

U.S. PATENT DOCUMENTS

| | | |
|---|---|---|
| 4,671,292 A | 6/1987 | Matzuk |
| 4,742,829 A | 5/1988 | Law et al. |
| 4,802,487 A | 2/1989 | Marti et al. |
| 4,869,258 A | 9/1989 | Hetz |
| 4,936,281 A | 6/1990 | Stasz |
| 5,000,185 A | 3/1991 | Yock |
| 5,036,855 A | 8/1991 | Fry et al. |
| 5,090,414 A | 2/1992 | Takano |
| 5,190,050 A | 3/1993 | Nitzsche |
| 5,269,301 A | 12/1993 | Cohen |
| 5,315,741 A | 5/1994 | Dubberke |
| 5,335,663 A | 8/1994 | Oakley et al. |
| 5,372,138 A | 12/1994 | Crowley et al. |
| 5,372,587 A | 12/1994 | Hammerslag et al. |
| 5,456,689 A | 10/1995 | Kresch et al. |
| 5,469,853 A | 11/1995 | Law et al. |
| 5,471,988 A | 12/1995 | Fujio et al. |
| 5,474,075 A | 12/1995 | Goldberg et al. |
| 5,492,126 A | 2/1996 | Hennige et al. |
| 5,514,130 A | 5/1996 | Baker |
| 5,527,331 A | 6/1996 | Kresch et al. |
| 5,531,676 A | 7/1996 | Edwards et al. |
| 5,607,389 A | 3/1997 | Edwards et al. |
| 5,649,911 A | 7/1997 | Trerotola |
| 5,662,664 A | 9/1997 | Gordon et al. |
| 5,662,680 A | 9/1997 | Desai |
| 5,666,954 A | 9/1997 | Chapelon et al. |
| 5,697,897 A | 12/1997 | Buchholtz et al. |
| 5,730,752 A | 3/1998 | Alden et al. |
| 5,741,287 A | 4/1998 | Alden et al. |
| 5,752,518 A | 5/1998 | Mcgee et al. |
| 5,769,795 A | 6/1998 | Terwilliger |
| 5,769,880 A | 6/1998 | Truckai et al. |
| 5,800,378 A | 9/1998 | Edwards et al. |
| 5,842,994 A | 12/1998 | Tenhoff et al. |
| 5,853,368 A | 12/1998 | Solomon et al. |
| 5,860,974 A | 1/1999 | Abele et al. |
| 5,863,294 A | 1/1999 | Alden |
| 5,865,729 A | 2/1999 | Meehan et al. |
| 5,873,828 A | 2/1999 | Fujio et al. |
| 5,876,340 A | 3/1999 | Tu et al. |
| 5,876,399 A | 3/1999 | Chia et al. |
| 5,891,137 A | 4/1999 | Chia et al. |
| 5,906,615 A | 5/1999 | Thompson |
| 5,908,385 A | 6/1999 | Chechelski et al. |
| 5,916,198 A | 6/1999 | Dillow |
| 5,931,787 A | 8/1999 | Dietz et al. |
| 5,957,941 A | 9/1999 | Ream |
| 5,964,740 A | 10/1999 | Ouchi |
| 5,979,452 A | 11/1999 | Fogarty et al. |
| 5,979,453 A | 11/1999 | Savage et al. |
| 5,984,942 A | 11/1999 | Alden et al. |
| 6,002,968 A | 12/1999 | Edwards |
| 6,007,499 A | 12/1999 | Martin et al. |
| 6,032,673 A | 3/2000 | Savage et al. |
| 6,039,748 A | 3/2000 | Savage et al. |
| 6,050,992 A | 4/2000 | Nichols |
| 6,055,449 A | 4/2000 | Navab |
| 6,059,766 A | 5/2000 | Greff |
| 6,077,257 A | 6/2000 | Edwards et al. |
| 6,080,150 A | 6/2000 | Gough |
| 6,083,169 A | 7/2000 | Hansen |
| 6,126,665 A | 10/2000 | Yoon |
| 6,141,577 A | 10/2000 | Rolland et al. |
| 6,146,378 A | 11/2000 | Mikus et al. |
| 6,146,380 A | 11/2000 | Racz et al. |
| 6,149,598 A | 11/2000 | Tanaka |
| 6,158,250 A | 12/2000 | Tibbals et al. |
| 6,171,249 B1 | 1/2001 | Chin et al. |
| 6,190,383 B1 | 2/2001 | Schmaltz et al. |
| 6,193,714 B1 | 2/2001 | Mcgaffigan et al. |
| 6,211,153 B1 | 4/2001 | Garnick et al. |
| 6,216,029 B1 | 4/2001 | Paltieli |
| 6,238,336 B1 | 5/2001 | Ouchi |
| 6,241,725 B1 | 6/2001 | Cosman |
| 6,254,601 B1 | 7/2001 | Burbank et al. |
| 6,261,234 B1 | 7/2001 | Lin |
| 6,280,441 B1 | 8/2001 | Ryan |
| 6,296,639 B1 | 10/2001 | Truckai et al. |
| 6,306,097 B1 | 10/2001 | Park et al. |
| 6,306,129 B1 | 10/2001 | Little et al. |
| 6,311,084 B1 | 10/2001 | Cormack et al. |
| 6,314,310 B1 | 11/2001 | Ben-Haim et al. |
| 6,315,730 B1 | 11/2001 | Hoff et al. |
| 6,315,741 B1 | 11/2001 | Martin et al. |
| 6,325,758 B1 | 12/2001 | Carol et al. |
| 6,336,899 B1 | 1/2002 | Yamazaki |
| 6,355,275 B1 | 3/2002 | Klein |
| 6,361,499 B1 | 3/2002 | Bates et al. |
| 6,368,280 B1 | 4/2002 | Cermak et al. |
| 6,379,348 B1 | 4/2002 | Onik |
| 6,405,732 B1 | 6/2002 | Edwards et al. |
| 6,419,048 B1 | 7/2002 | Robinson et al. |
| 6,419,648 B1 | 7/2002 | Vitek et al. |
| 6,419,653 B2 | 7/2002 | Edwards et al. |
| 6,419,673 B1 | 7/2002 | Edwards et al. |
| 6,425,867 B1 | 7/2002 | Vaezy et al. |
| 6,432,067 B1 | 8/2002 | Martin et al. |
| 6,443,902 B1 | 9/2002 | Sasady |
| 6,447,477 B2 | 9/2002 | Burney et al. |
| 6,461,296 B1 | 10/2002 | Desai |
| 6,463,331 B1 | 10/2002 | Edwards |
| 6,468,228 B1 | 10/2002 | Topel et al. |
| 6,475,152 B1 | 11/2002 | Kelly, Jr. et al. |

(56) References Cited

U.S. PATENT DOCUMENTS

| | | |
|---|---|---|
| 6,482,203 B2 | 11/2002 | Paddock et al. |
| 6,485,413 B1 | 11/2002 | Boppart et al. |
| 6,506,154 B1 | 1/2003 | Ezion et al. |
| 6,506,156 B1 | 1/2003 | Jones et al. |
| 6,506,171 B1 | 1/2003 | Vitek et al. |
| 6,507,747 B1 | 1/2003 | Gowda et al. |
| 6,508,815 B1 | 1/2003 | Strul et al. |
| 6,522,142 B1 | 2/2003 | Freundlich |
| 6,526,320 B2 | 2/2003 | Mitchell |
| 6,540,677 B1 | 4/2003 | Angelsen et al. |
| 6,543,272 B1 | 4/2003 | Vitek |
| 6,544,176 B2 | 4/2003 | Mikus et al. |
| 6,550,482 B1 | 4/2003 | Burbank et al. |
| 6,553,013 B1 | 4/2003 | Jones et al. |
| 6,554,780 B1 | 4/2003 | Sampson et al. |
| 6,554,801 B1 | 4/2003 | Steward et al. |
| 6,559,644 B2 | 5/2003 | Froundlich et al. |
| 6,569,159 B1 | 5/2003 | Edwards et al. |
| 6,572,613 B1 | 6/2003 | Ellman et al. |
| 6,575,969 B1 | 6/2003 | Rittman, III |
| 6,579,298 B1 | 6/2003 | Bruneau et al. |
| 6,585,694 B1 | 7/2003 | Smith et al. |
| 6,589,237 B2 | 7/2003 | Woloszko et al. |
| 6,589,238 B2 | 7/2003 | Edwards et al. |
| 6,592,559 B1 | 7/2003 | Pakter et al. |
| 6,602,251 B2 | 8/2003 | Burbank et al. |
| 6,610,054 B1 | 8/2003 | Edwards et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,623,481 B1 | 9/2003 | Garbagnati et al. |
| 6,626,832 B1 | 9/2003 | Paltieli et al. |
| 6,626,854 B2 | 9/2003 | Friedman et al. |
| 6,626,855 B1 | 9/2003 | Weng et al. |
| 6,632,193 B1 | 10/2003 | Davison et al. |
| 6,635,055 B1 | 10/2003 | Cronin |
| 6,635,065 B2 | 10/2003 | Burbank et al. |
| 6,638,275 B1 | 10/2003 | Mcgaffigan et al. |
| 6,638,286 B1 | 10/2003 | Burbank et al. |
| 6,645,162 B2 | 11/2003 | Friedman et al. |
| 6,645,202 B1 | 11/2003 | Pless et al. |
| 6,652,516 B1 | 11/2003 | Gough |
| 6,654,202 B2 | 11/2003 | Rea et al. |
| 6,660,002 B1 | 12/2003 | Edwards et al. |
| 6,660,024 B1 | 12/2003 | Flaherty et al. |
| 6,662,680 B2 | 12/2003 | Rocket |
| 6,663,624 B2 | 12/2003 | Edwards et al. |
| 6,663,626 B2 | 12/2003 | Truckai et al. |
| 6,666,833 B1 | 12/2003 | Friedman et al. |
| 6,669,643 B1 | 12/2003 | Dubinsky |
| 6,679,855 B2 | 1/2004 | Horn et al. |
| 6,685,639 B1 | 2/2004 | Wang et al. |
| 6,689,128 B2 | 2/2004 | Sliwa et al. |
| 6,692,490 B1 | 2/2004 | Edwards |
| 6,695,786 B2 | 2/2004 | Wang et al. |
| 6,701,931 B2 | 3/2004 | Sliwa et al. |
| 6,705,994 B2 | 3/2004 | Vortman et al. |
| 6,712,815 B2 | 3/2004 | Sampson et al. |
| 6,716,184 B2 | 4/2004 | Vaezy et al. |
| 6,719,755 B2 | 4/2004 | Sliwa et al. |
| 6,728,571 B1 | 4/2004 | Barbato |
| 6,730,081 B1 | 5/2004 | Desai |
| 6,733,458 B1 | 5/2004 | Steins et al. |
| 6,735,461 B2 | 5/2004 | Vitek et al. |
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,786,870 B2 | 9/2004 | Miyaki et al. |
| 6,790,180 B2 | 9/2004 | Vitek |
| 6,798,716 B1 | 9/2004 | Charych |
| 6,805,128 B1 | 10/2004 | Pless et al. |
| 6,805,129 B1 | 10/2004 | Pless et al. |
| 6,813,520 B2 | 11/2004 | Truckai et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,899,712 B2 | 5/2005 | Moutafis et al. |
| 6,908,433 B1 | 6/2005 | Pruter |
| 6,921,398 B2 | 7/2005 | Carmel et al. |
| 6,923,807 B2 | 8/2005 | Ryan et al. |
| 6,936,048 B2 | 8/2005 | Hurst |
| 6,938,048 B1 | 8/2005 | Jilk et al. |
| 6,944,490 B1 | 9/2005 | Chow |
| 6,953,458 B2 | 10/2005 | Loeb |
| 6,969,354 B1 | 11/2005 | Marian |
| 6,994,706 B2 | 2/2006 | Chornenky et al. |
| 7,101,387 B2 | 9/2006 | Garabedian et al. |
| 7,160,296 B2 | 1/2007 | Pearson et al. |
| 7,166,075 B2 | 1/2007 | Varghese et al. |
| 7,171,255 B2 | 1/2007 | Holupka et al. |
| 7,229,401 B2 | 6/2007 | Kindlein |
| 7,241,293 B2 | 7/2007 | Davison |
| 7,247,141 B2 | 7/2007 | Makin et al. |
| 7,276,063 B2 | 10/2007 | Davison et al. |
| 7,306,595 B2 | 12/2007 | Ostrovsky et al. |
| 7,317,988 B2 | 1/2008 | Johnson |
| 7,331,957 B2 | 2/2008 | Woloszko et al. |
| 7,333,844 B2 | 2/2008 | Jones et al. |
| 7,387,628 B1 | 6/2008 | Behl et al. |
| 7,517,346 B2 | 4/2009 | Sloan et al. |
| 7,549,424 B2 | 6/2009 | Desai |
| 7,771,357 B2 | 8/2010 | Burbank et al. |
| 7,815,571 B2 | 10/2010 | Deckman et al. |
| 7,874,986 B2 | 1/2011 | Deckman et al. |
| 7,918,795 B2 | 4/2011 | Grossman |
| 7,963,941 B2 | 6/2011 | Wilk |
| 8,080,009 B2 | 12/2011 | Lee et al. |
| 8,088,072 B2 | 1/2012 | Munrow et al. |
| 8,157,741 B2 | 4/2012 | Hirota |
| 8,157,745 B2 | 4/2012 | Schoot |
| 8,206,300 B2 | 6/2012 | Deckman et al. |
| 8,216,231 B2 | 7/2012 | Behl et al. |
| 8,221,321 B2 | 7/2012 | McMorrow et al. |
| 8,262,574 B2 | 9/2012 | Placek et al. |
| 8,262,577 B2 | 9/2012 | Munrow et al. |
| 8,287,485 B2 | 10/2012 | Kimura et al. |
| 8,298,145 B2 | 10/2012 | Deckman et al. |
| 8,337,434 B2 | 12/2012 | Vaezy et al. |
| 8,377,041 B2 | 2/2013 | Frassica et al. |
| 8,469,893 B2 | 6/2013 | Chiang et al. |
| 8,506,485 B2 | 8/2013 | Deckman et al. |
| 8,512,330 B2 | 8/2013 | Epstein et al. |
| 8,512,333 B2 | 8/2013 | Epstein et al. |
| 8,540,634 B2 | 9/2013 | Bruce et al. |
| 8,585,598 B2 | 11/2013 | Razzaque et al. |
| 8,622,911 B2 | 1/2014 | Hossack et al. |
| 8,663,130 B2 | 3/2014 | Neubach et al. |
| 8,718,339 B2 | 5/2014 | Tonomura et al. |
| 8,814,796 B2 | 8/2014 | Martin et al. |
| 8,845,559 B2 | 9/2014 | Darlington et al. |
| 8,900,225 B2 | 12/2014 | Bar-Tal et al. |
| 8,992,427 B2 | 3/2015 | Munrow et al. |
| 9,089,287 B2 | 7/2015 | Sliwa et al. |
| 9,119,649 B2 | 9/2015 | Van der Weide et al. |
| 9,198,707 B2 | 12/2015 | McKay et al. |
| 9,198,719 B2 | 12/2015 | Murdeshwar et al. |
| 9,247,925 B2 | 2/2016 | Havel et al. |
| 9,357,977 B2 | 6/2016 | Grossman |
| 9,439,627 B2 | 9/2016 | Case et al. |
| 9,460,563 B2 | 10/2016 | Merschon et al. |
| 9,510,898 B2 | 12/2016 | Epstein et al. |
| 9,516,996 B2 | 12/2016 | Diolaiti et al. |
| 9,517,047 B2 | 12/2016 | Grossman |
| 9,662,166 B2 | 5/2017 | Lee et al. |
| 9,808,310 B2 | 11/2017 | Grossman |
| 9,861,336 B2 | 1/2018 | Munrow et al. |
| 9,987,080 B2 | 6/2018 | Grossman et al. |
| 10,058,342 B2 | 8/2018 | Deckman et al. |
| 10,182,862 B2 | 1/2019 | Grossman et al. |
| 10,321,951 B2 | 6/2019 | Placek et al. |
| 10,595,819 B2 | 3/2020 | Deckman et al. |
| 10,856,838 B2 | 12/2020 | Munrow et al. |

(56) References Cited

U.S. PATENT DOCUMENTS

| | | |
|---|---|---|
| 10,993,770 B2 | 5/2021 | Hammudi et al. |
| 11,096,760 B2 | 8/2021 | Munrow et al. |
| 11,096,761 B2 | 8/2021 | Munrow et al. |
| 11,219,483 B2 | 1/2022 | Chen et al. |
| 11,259,825 B2 | 3/2022 | Deckman et al. |
| 11,419,668 B2 | 8/2022 | Grossman |
| 11,419,682 B2 | 8/2022 | Hammudi et al. |
| 11,564,735 B2 | 1/2023 | Placek et al. |
| 11,583,243 B2 | 2/2023 | Munrow et al. |
| 11,612,431 B2 | 3/2023 | Chen |
| 2001/0007940 A1 | 7/2001 | Tu et al. |
| 2001/0014805 A1 | 8/2001 | Burbank et al. |
| 2001/0035189 A1 | 11/2001 | Dobak et al. |
| 2001/0051802 A1 | 12/2001 | Woloszko et al. |
| 2002/0002393 A1 | 1/2002 | Mitchell |
| 2002/0022835 A1 | 2/2002 | Lee |
| 2002/0040220 A1 | 4/2002 | Zvuloni et al. |
| 2002/0052600 A1 | 5/2002 | Davison et al. |
| 2002/0068871 A1 | 6/2002 | Mendlein et al. |
| 2002/0072742 A1 | 6/2002 | Schaefer et al. |
| 2002/0077550 A1 | 6/2002 | Rabiner et al. |
| 2002/0124853 A1* | 9/2002 | Burbank .......... A61B 17/282 128/898 |
| 2002/0156373 A1 | 10/2002 | Wakabayashi et al. |
| 2002/0183735 A1 | 12/2002 | Edwards et al. |
| 2003/0009164 A1 | 1/2003 | Woloszko et al. |
| 2003/0009166 A1 | 1/2003 | Moutafis et al. |
| 2003/0014046 A1 | 1/2003 | Edwards et al. |
| 2003/0028111 A1 | 2/2003 | Vaezy et al. |
| 2003/0032896 A1 | 2/2003 | Bosley et al. |
| 2003/0045768 A1 | 3/2003 | Hirooka et al. |
| 2003/0078502 A1 | 4/2003 | Miyaki et al. |
| 2003/0114732 A1 | 6/2003 | Webler et al. |
| 2003/0130575 A1 | 7/2003 | Desai |
| 2003/0130655 A1 | 7/2003 | Woloszko et al. |
| 2003/0130665 A1 | 7/2003 | Pinczewski et al. |
| 2003/0195420 A1 | 10/2003 | Mendlein et al. |
| 2003/0195496 A1 | 10/2003 | Maguire et al. |
| 2003/0195502 A1 | 10/2003 | Garabedian et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0006336 A1 | 1/2004 | Swanson |
| 2004/0030268 A1 | 2/2004 | Weng et al. |
| 2004/0049121 A1 | 3/2004 | Yaron |
| 2004/0054366 A1 | 3/2004 | Davison et al. |
| 2004/0064134 A1 | 4/2004 | Xiao et al. |
| 2004/0082883 A1 | 4/2004 | Kohno |
| 2004/0120668 A1 | 6/2004 | Loeb |
| 2004/0147920 A1 | 7/2004 | Keidar et al. |
| 2004/0153057 A1 | 8/2004 | Davison |
| 2004/0175399 A1 | 9/2004 | Schiffman et al. |
| 2004/0176760 A1 | 9/2004 | Qiu |
| 2004/0193028 A1 | 9/2004 | Jones et al. |
| 2004/0193238 A1 | 9/2004 | Mosher et al. |
| 2004/0199179 A1 | 10/2004 | Elliott |
| 2004/0215182 A1 | 10/2004 | Lee |
| 2004/0230190 A1 | 11/2004 | Dahla et al. |
| 2004/0231772 A1 | 11/2004 | Leonard et al. |
| 2004/0254572 A1 | 12/2004 | Mcintyre et al. |
| 2005/0033108 A1 | 2/2005 | Sawyer |
| 2005/0033160 A1 | 2/2005 | Yamagata et al. |
| 2005/0038340 A1 | 2/2005 | Vaezy et al. |
| 2005/0085718 A1 | 4/2005 | Shahidi |
| 2005/0085730 A1 | 4/2005 | Flesch et al. |
| 2005/0096647 A1 | 5/2005 | Steinke et al. |
| 2005/0107781 A1 | 5/2005 | Ostrovsky et al. |
| 2005/0124882 A1 | 6/2005 | Ladabaum et al. |
| 2005/0149013 A1 | 7/2005 | Lee |
| 2005/0159676 A1 | 7/2005 | Taylor et al. |
| 2005/0177209 A1 | 8/2005 | Leung et al. |
| 2005/0197577 A1 | 9/2005 | Makin et al. |
| 2005/0203399 A1* | 9/2005 | Vaezy .......... A61B 8/08 600/439 |
| 2005/0203410 A1 | 9/2005 | Jenkins |
| 2005/0215990 A1 | 9/2005 | Govari |
| 2005/0216039 A1 | 9/2005 | Lederman |
| 2005/0228288 A1 | 10/2005 | Hurst |
| 2005/0240126 A1 | 10/2005 | Foley et al. |
| 2005/0255039 A1 | 11/2005 | Desai |
| 2005/0256405 A1 | 11/2005 | Makin et al. |
| 2006/0010207 A1 | 1/2006 | Akerman et al. |
| 2006/0015115 A1 | 1/2006 | Haines |
| 2006/0018665 A1 | 1/2006 | Shibata et al. |
| 2006/0020204 A1 | 1/2006 | Serra et al. |
| 2006/0058671 A1 | 3/2006 | Vitek et al. |
| 2006/0058680 A1 | 3/2006 | Solomon |
| 2006/0089636 A1 | 4/2006 | Christopherson et al. |
| 2006/0178560 A1 | 8/2006 | Saadat et al. |
| 2006/0178665 A1 | 8/2006 | Sloan et al. |
| 2006/0184049 A1 | 8/2006 | Tsujita |
| 2006/0189972 A1* | 8/2006 | Grossman .......... A61B 18/1477 606/41 |
| 2006/0241368 A1 | 10/2006 | Fichtinger et al. |
| 2006/0264758 A1 | 11/2006 | Hossack et al. |
| 2006/0276811 A1 | 12/2006 | Copa et al. |
| 2006/0285637 A1 | 12/2006 | Varjonen et al. |
| 2006/0287579 A1 | 12/2006 | Okada |
| 2007/0006215 A1 | 1/2007 | Epstein et al. |
| 2007/0016183 A1 | 1/2007 | Lee et al. |
| 2007/0083082 A1 | 4/2007 | Kiser et al. |
| 2007/0088247 A1 | 4/2007 | Bliweis et al. |
| 2007/0112306 A1 | 5/2007 | Agnew |
| 2007/0123797 A1 | 5/2007 | Krause |
| 2007/0161897 A1 | 7/2007 | Sasaki et al. |
| 2007/0161905 A1 | 7/2007 | Munrow |
| 2007/0167762 A1 | 7/2007 | Kim et al. |
| 2007/0167806 A1* | 7/2007 | Wood .......... A61B 6/032 600/459 |
| 2007/0167808 A1 | 7/2007 | Nozaki |
| 2007/0203486 A1 | 8/2007 | Young |
| 2007/0208327 A1 | 9/2007 | Rosemberg et al. |
| 2007/0232913 A1 | 10/2007 | Lau et al. |
| 2007/0239062 A1 | 10/2007 | Chopra et al. |
| 2007/0255267 A1* | 11/2007 | Diederich .......... A61N 7/022 606/41 |
| 2008/0015664 A1 | 1/2008 | Podhajsky |
| 2008/0045793 A1 | 2/2008 | Humble et al. |
| 2008/0051629 A1 | 2/2008 | Sugiyama et al. |
| 2008/0147056 A1 | 6/2008 | Van et al. |
| 2008/0171940 A1 | 7/2008 | McGahan |
| 2008/0188916 A1 | 8/2008 | Jones et al. |
| 2008/0228081 A1 | 9/2008 | Becker et al. |
| 2009/0043295 A1 | 2/2009 | Arnal et al. |
| 2009/0093718 A1 | 4/2009 | Jibiki et al. |
| 2009/0099544 A1 | 4/2009 | Munrow et al. |
| 2009/0118613 A1 | 5/2009 | Krugman et al. |
| 2009/0131790 A1 | 5/2009 | Munrow et al. |
| 2009/0171218 A1 | 7/2009 | Nygaard et al. |
| 2009/0287081 A1 | 11/2009 | Grossman et al. |
| 2010/0056926 A1 | 3/2010 | Deckman et al. |
| 2010/0081920 A1 | 4/2010 | Whitmore, III |
| 2010/0160781 A1 | 6/2010 | Carter et al. |
| 2010/0160787 A1 | 6/2010 | Gorzitze |
| 2010/0262133 A1 | 10/2010 | Hoey et al. |
| 2010/0268067 A1 | 10/2010 | RaZZaque et al. |
| 2010/0286687 A1 | 11/2010 | Feldberg et al. |
| 2010/0305439 A1 | 12/2010 | Shai et al. |
| 2011/0022034 A1 | 1/2011 | Wilson et al. |
| 2011/0028847 A1 | 2/2011 | Whitmore, III |
| 2011/0046483 A1 | 2/2011 | Fuchs et al. |
| 2011/0046552 A1 | 2/2011 | Bankiewicz et al. |
| 2011/0087100 A1* | 4/2011 | Grossman .......... A61B 18/1477 600/439 |
| 2011/0098564 A1 | 4/2011 | Larson et al. |
| 2011/0208061 A1 | 8/2011 | Chang |
| 2011/0218444 A1 | 9/2011 | Steffen et al. |
| 2011/0238057 A1 | 9/2011 | Moss et al. |
| 2011/0276038 A1* | 11/2011 | McIntyre .......... A61B 17/42 606/1 |
| 2011/0288540 A1 | 11/2011 | Wright et al. |
| 2012/0010479 A1 | 1/2012 | Eusemann et al. |
| 2012/0035464 A1 | 2/2012 | Raju et al. |

(56) References Cited

U.S. PATENT DOCUMENTS

| | | |
|---|---|---|
| 2012/0071794 A1 | 3/2012 | Karni |
| 2012/0165813 A1 | 6/2012 | Lee et al. |
| 2012/0209115 A1 | 8/2012 | Tonomura |
| 2012/0245575 A1* | 9/2012 | Epstein .............. A61B 18/1487 606/33 |
| 2012/0266874 A1* | 10/2012 | Kawakami ........... A61G 10/023 128/202.12 |
| 2012/0271277 A1 | 10/2012 | Fischell et al. |
| 2012/0277737 A1 | 11/2012 | Curley |
| 2012/0289858 A1 | 11/2012 | Ouyang et al. |
| 2012/0316440 A1 | 12/2012 | Munrow et al. |
| 2013/0041259 A1 | 2/2013 | Harks et al. |
| 2013/0085497 A1 | 4/2013 | Chang et al. |
| 2013/0137979 A1 | 5/2013 | Deckman et al. |
| 2013/0225995 A1 | 8/2013 | Hashiguchi et al. |
| 2013/0281863 A1 | 10/2013 | Chiang et al. |
| 2013/0296699 A1 | 11/2013 | Deckman et al. |
| 2013/0317366 A1 | 11/2013 | Hirayama et al. |
| 2014/0011172 A1* | 1/2014 | Lowe ................... G09B 23/288 434/273 |
| 2014/0180273 A1 | 6/2014 | Nair |
| 2014/0276081 A1 | 9/2014 | Tegels |
| 2014/0316434 A1 | 10/2014 | Simaan et al. |
| 2015/0094712 A1 | 4/2015 | Murdeshwar et al. |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2016/0030240 A1 | 2/2016 | Gonenc et al. |
| 2016/0051221 A1 | 2/2016 | Dickhans et al. |
| 2016/0113621 A1 | 4/2016 | Deckman et al. |
| 2016/0151041 A1 | 6/2016 | Lee et al. |
| 2016/0249878 A1 | 9/2016 | Grossman |
| 2016/0278740 A1 | 9/2016 | Negrila et al. |
| 2016/0310042 A1 | 10/2016 | Kesten et al. |
| 2017/0060674 A1 | 3/2017 | Nazari et al. |
| 2017/0100106 A1 | 4/2017 | Jinno |
| 2017/0245838 A1 | 8/2017 | Munrow et al. |
| 2017/0245891 A1 | 8/2017 | Munrow et al. |
| 2017/0290626 A1 | 10/2017 | Deckman et al. |
| 2017/0290627 A1 | 10/2017 | Deckman et al. |
| 2018/0042572 A1 | 2/2018 | Munrow et al. |
| 2018/0070916 A9 | 3/2018 | Deckman et al. |
| 2018/0078303 A1 | 3/2018 | Grossman |
| 2018/0132927 A1 | 5/2018 | Chen et al. |
| 2018/0289430 A1 | 10/2018 | Kahya et al. |
| 2018/0318026 A1 | 11/2018 | Placek |
| 2019/0133696 A1 | 5/2019 | Spero |
| 2019/0192217 A1 | 6/2019 | Grossman |
| 2019/0336101 A1 | 11/2019 | Chiang et al. |
| 2019/0350648 A1 | 11/2019 | Owens et al. |
| 2020/0229892 A1 | 7/2020 | Munrow et al. |
| 2021/0000565 A1 | 1/2021 | Munrow et al. |
| 2021/0015450 A1 | 1/2021 | Deckman et al. |
| 2021/0038341 A1 | 2/2021 | Munrow et al. |
| 2021/0186455 A1 | 6/2021 | Munrow et al. |
| 2021/0228179 A1 | 7/2021 | Munrow et al. |
| 2021/0338365 A1 | 11/2021 | Munrow et al. |
| 2021/0346095 A1 | 11/2021 | Hammudi et al. |
| 2022/0175405 A1 | 6/2022 | Deckman et al. |
| 2022/0265381 A1 | 8/2022 | Munrow et al. |
| 2022/0346866 A1 | 11/2022 | Grossman |

FOREIGN PATENT DOCUMENTS

| | | |
|---|---|---|
| CN | 102238921 A | 11/2011 |
| CN | 102449666 A | 5/2012 |
| CN | 102470013 A | 5/2012 |
| CN | 103379853 A | 10/2013 |
| CN | 103417293 A | 12/2013 |
| CN | 104619263 A | 5/2015 |
| CN | 104812433 A | 7/2015 |
| CN | 105007815 A | 10/2015 |
| EP | 1132049 A1 | 9/2001 |
| EP | 1426011 A1 | 6/2004 |
| EP | 1649822 A1 | 4/2006 |
| JP | H01157713 U | 10/1989 |
| JP | H07306714 A | 11/1995 |
| JP | H1176254 A | 3/1999 |
| JP | H11508790 A | 8/1999 |
| JP | 2000342587 A | 12/2000 |
| JP | 2001340350 A | 12/2001 |
| JP | 2003144436 A | 5/2003 |
| JP | 2003534037 A | 11/2003 |
| JP | 2004041580 A | 2/2004 |
| JP | 2005058584 A | 3/2005 |
| JP | 2005323669 A | 11/2005 |
| JP | 2006513831 A | 4/2006 |
| JP | 2006255405 A | 9/2006 |
| JP | 2006346341 A | 12/2006 |
| JP | 2007144180 A | 6/2007 |
| JP | 2007215672 A | 8/2007 |
| JP | 2007244857 A | 9/2007 |
| JP | 2007-312798 | 12/2007 |
| JP | 2007536063 A | 12/2007 |
| JP | 2009-505768 | 2/2009 |
| JP | 2009022764 A | 2/2009 |
| JP | 2009136523 A | 6/2009 |
| JP | 2009526554 A | 7/2009 |
| JP | 2011500164 A | 1/2011 |
| JP | 2011-0188046 | 9/2011 |
| JP | 2012519037 A | 8/2012 |
| JP | 2012-176239 | 9/2012 |
| JP | 2012-228286 | 11/2012 |
| JP | 2013500778 A | 1/2013 |
| JP | 2013527782 A | 7/2013 |
| JP | 2013529943 A | 7/2013 |
| JP | 2013-153883 | 8/2013 |
| JP | 2015528114 A | 9/2015 |
| JP | 2015-529114 | 10/2015 |
| JP | 2016-159068 | 9/2016 |
| JP | 6343648 B2 | 6/2018 |
| KR | 2014-0103690 A | 8/2014 |
| RU | 2012358 C1 | 5/1994 |
| WO | WO 1995/28129 | 10/1995 |
| WO | WO 1997/17105 | 5/1997 |
| WO | WO 1998/11834 | 3/1998 |
| WO | WO 1998/14169 | 4/1998 |
| WO | WO 1999/27837 | 6/1999 |
| WO | WO 1999/33394 | 7/1999 |
| WO | WO 1999/43366 | 9/1999 |
| WO | WO 2000/00098 | 1/2000 |
| WO | WO 2001/13782 | 3/2001 |
| WO | WO 01/66178 A1 | 9/2001 |
| WO | WO 2001/80723 | 11/2001 |
| WO | WO 2001/95819 | 12/2001 |
| WO | WO 2002/11639 | 2/2002 |
| WO | WO 02/089686 A1 | 11/2002 |
| WO | WO 2003/005882 | 1/2003 |
| WO | WO 03/049630 A2 | 6/2003 |
| WO | WO 2003/065908 | 8/2003 |
| WO | WO 2003/088833 | 10/2003 |
| WO | WO 2004/002293 | 1/2004 |
| WO | WO 2004/002550 | 1/2004 |
| WO | WO 2004/020011 | 3/2004 |
| WO | WO 2004/035110 | 4/2004 |
| WO | WO 2004/058328 | 7/2004 |
| WO | WO 2004/064658 | 8/2004 |
| WO | WO 2004/112446 A1 | 12/2004 |
| WO | WO 2005/110255 | 11/2005 |
| WO | WO 2006/042117 | 4/2006 |
| WO | WO 2006/086234 A3 | 8/2006 |
| WO | WO 2006/089426 | 8/2006 |
| WO | WO 2007/005830 | 1/2007 |
| WO | WO 2007/112144 | 10/2007 |
| WO | WO 2007/124265 | 11/2007 |
| WO | WO 2007/144004 | 12/2007 |
| WO | WO 2007/149595 | 12/2007 |
| WO | WO 2008/016922 | 2/2008 |
| WO | WO 2008/144341 | 11/2008 |
| WO | WO 2009/027890 A1 | 3/2009 |
| WO | WO 2009/049082 | 4/2009 |
| WO | WO 2009/158012 | 12/2009 |
| WO | WO 2010/027820 | 3/2010 |

(56) References Cited

FOREIGN PATENT DOCUMENTS

| WO | WO 2010/099481 | 9/2010 |
|---|---|---|
| WO | WO 2014/009810 A3 | 1/2014 |
| WO | WO 2014/039795 | 3/2014 |
| WO | WO 2015/087203 | 6/2015 |
| WO | WO 2015/110946 | 7/2015 |
| WO | WO 2017/132153 | 8/2017 |
| WO | WO 2018/089523 | 5/2018 |
| WO | WO 2018/089923 | 5/2018 |
| WO | WO 2018/201158 | 11/2018 |
| WO | WO 2018/204284 | 11/2018 |
| WO | WO 2019/226452 | 11/2019 |
| WO | WO 2022/093848 A1 | 5/2022 |

OTHER PUBLICATIONS

U.S. Appl. No. 12/973,642 (U.S. Pat. No. 9,808,310), Method and Device for Uterine Fibroid Treatment, filed Dec. 20, 2010 (Nov. 7, 2017).
U.S. Appl. No. 15/720,199 (U.S. Pat. No. 9,987,080), Method and Device for Uterine Fibroid Treatment, filed Sep. 29, 2017 (Jun. 5, 2018).
U.S. Appl. No. 15/970,428 (U.S. Pat. No. 10,182,862), Method and Device for Uterine Fibroid Treatment, filed May 3, 2018 (Jan. 22, 2019).
U.S. Appl. No. 16/221,138, Method and Device for Uterine Fibroid Treatment, filed Dec. 14, 2018.
U.S. Appl. No. 11/620,569, Intrauterine Ultrasound and Method for Use, filed Jan. 5, 2007.
U.S. Appl. No. 11/620,594 (U.S. Pat. No. 9,357,977), Interventional Deployment And Imaging System, filed Jan. 5, 2007 (Jun. 7, 2016).
U.S. Appl. No. 15/150,813 (U.S. Pat. No. 9,517,047), Interventional Deployment And Imaging System, filed May 10, 2016 (Dec. 13, 2016).
U.S. Appl. No. 13/667,891 (U.S. Pat. No. 10,058,342), Devices and Methods for Treatment of Tissue, filed Nov. 2, 2012 (Aug. 28, 2018).
U.S. Appl. No. 15/628,166, Devices and Methods for Treatment of Tissue, filed Jun. 20, 2017.
U.S. Appl. No. 15/634,368, Devices and Methods for Treatment of Tissue, filed Jun. 27, 2017.
U.S. Appl. No. 15/824,511, Interventional Deployment and Imaging System, filed Nov. 28, 2017.
U.S. Appl. No. 11/409,496 (U.S. Pat. No. 7,815,571), Rigid Delivery Systems Having Inclined Ultrasound and Needle, filed Apr. 20, 2006 (Oct. 19, 2010).
U.S. Appl. No. 11/564,164 (U.S. Pat. No. 7,874,986), Methods and Devices for Visualization and Ablation of Tissue, filed Nov. 18, 2006 (Jan. 25, 2011).
U.S. Appl. No. 12/973,587 (U.S. Pat. No. 8,506,485), Devices and Methods for Treatment of Tissue, filed Dec. 20, 2010 (Aug. 13, 2013).
U.S. Appl. No. 13/484,076 (U.S. Pat. No. 10,595,819), Ablation Device With Articulated Imaging Transducer, filed May 30, 2012 (Mar. 24, 2020).
U.S. Appl. No. 14/989,732 (U.S. Pat. No. 10,610,197), Ablation Device With Articulated Imaging Transducer, filed Mar. 15, 2018 (Apr. 7, 2020).
U.S. Appl. No. 16/782,477, Ablation Device With Articulated Imaging Transducer, filed Feb. 5, 2020.
U.S. Appl. No. 11/775,452 (U.S. Pat. No. 8,298,145), Peri-Capsular Fibroid Treatment, filed Jul. 10, 2007 (Oct. 30, 2012).
U.S. Appl. No. 12/119,147, Systems and Methods for Deploying Echogenic Components in Ultrasonic Imaging Fields, filed May 12, 2008.
U.S. Appl. No. 12/245,567 (U.S. Pat. No. 8,088,072), Methods and Systems for Controlled Deployment of Needles in Tissue, filed Oct. 3, 2008 (Jan. 3, 2012).
U.S. Appl. No. 13/307,304 (U.S. Pat. No. 8,262,577), Methods and Systems for Controlled Deployment of Needles in Tissue, filed Nov. 30, 2011 (Sep. 11, 2012).
U.S. Appl. No. 13/589,975, Methods and Systems for Controlled Deployment of Needles in Tissue, filed Aug. 20, 2012.
U.S. Appl. No. 15/595,659, Methods and Systems for Controlled Deployment of Needles in Tissue, filed May 15, 2017.
U.S. Appl. No. 15/597,511, Methods and Systems for Controlled Deployment of Needles in Tissue, filed May 17, 2017.
U.S. Appl. No. 16/841,201, Methods and Systems for Controlled Deployment of Needles in Tissue, filed Apr. 6, 2020.
U.S. Appl. No. 17/028,593, Methods and Systems for Controlled Deployment of Needles in Tissue, filed Sep. 22, 2020.
U.S. Appl. No. 17/028,596, Methods and Systems for Controlled Deployment of Needles in Tissue, filed Sep. 22, 2020.
U.S. Appl. No. 17/376,039, Methods and Systems for Controlled Deployment of Needles in Tissue, filed Jul. 14, 2021.
U.S. Appl. No. 12/424,357, Submucosal Fibroid Ablation for the Treatment of Menorrhagia, filed Apr. 15, 2009.
U.S. Appl. No. 12/198,861, Ablation Device With Articulated Imaging Transducer, filed Aug. 26, 2008.
U.S. Appl. No. 12/198,861 (U.S. Pat. No. 8,206,300), Ablation Device With Articulated Imaging Transducer, filed Feb. 8, 2011 (Jun. 26, 2012).
U.S. Appl. No. 12/712,969 (U.S. Pat. No. 8,262,574), Needle and Tine Deployment Mechanism, filed Feb. 25, 2010 (Sep. 11, 2012).
U.S. Appl. No. 13/589,956 (U.S. Pat. No. 10,321,951), Needle and Tine Deployment Mechanism, filed Aug. 20, 2012 (Jun. 18, 2019).
U.S. Appl. No. 16/417,193, Needle and Tine Deployment Mechanism, filed May 20, 2019.
U.S. Appl. No. 12/775,257, Dual Energy Therapy Needle, filed May 6, 2010.
U.S. Appl. No. 13/801,782 (U.S. Pat. No. 9,861,336), Method and Systems for Controlled Deployment of Needle Structures in Tissue, filed Mar. 13, 2013 (Jan. 9, 2018).
U.S. Appl. No. 15/793,874 (U.S. Pat. No. 10,856,838), Method and Systems for Controlled Deployment of Needle Structures in Tissue, filed Oct. 25, 2017 (Dec. 8, 2020).
U.S. Appl. No. 17/084,141, Method and Systems for Controlled Deployment of Needle Structures in Tissue, filed Oct. 29, 2020.
U.S. Appl. No. 17/232,051, Method and Systems for Controlled Deployment of Needle Structures in Tissue, filed Apr. 15, 2021.
U.S. Appl. No. 13/801,840 (U.S. Pat. No. 8,992,427), Method and Systems for Controlled Deployment of Needle Structures in Tissue, filed Mar. 13, 2013 (Mar. 31, 2015).
U.S. Appl. No. 16/037,548, Disposable Sheath for Ultrasound Probe Mounted on Reusable Needle Structure, filed Jul. 17, 2018.
U.S. Appl. No. 16/408,790 (U.S. Pat. No. 10,993,770), Controlled Treatment of Tissue and Dynamic Interaction With, and Comparison of, Tissue and/or Treatment Data, filed May 10, 2019 (May 4, 2021).
U.S. Appl. No. 17/233,838, Controlled Treatment of Tissue And Dynamic Interaction With, and Comparison of, Tissue and/or Treatment Data, filed Apr. 19, 2021.
U.S. Appl. No. 15/811,520, Methods and Systems for Real-Time Planning and Monitoring of Ablation Needle Deployment in Tissue, filed Nov. 13, 2017.
U.S. Appl. No. 10/345,635 (U.S. Pat. No. 6,936,048), Echogenic Needle for Transvaginal Ultrasound Directed Reduction of Uterine Fibroids and an Associated Method, filed Jan. 16, 2003 (Aug. 30, 2005).
U.S. Appl. No. 11/142,952, Echogenic Needle for Transvaginal Ultrasound Directed Reduction of Uterine Fibroids and an Associated Method, U.S. Appl. No. 11/142,952.
U.S. Appl. No. 16/414,040, Methods and Systems for In Situ Exchange, filed May 16, 2019.
U.S. Appl. No. 16/666,271, Methods for Monitoring Ablation Progress With Doppler Ultrasound, filed Oct. 28, 2019.
Alterovitz, et al. Simulating Needle Insertion and Radioactive Seed Implantation for Prostate Brachytherapy. Medicine Meets Virtual Reality 11, Westwood et al. (Eds.), IOS Press, Jan. 2003, pp. 19-25.

(56) References Cited

OTHER PUBLICATIONS

Bergamini, et al. Laparoscopic Radiofrequency Thermal Ablation: A New Approach to Symptomatic Uterine Myomas. Am. J. Obstetrics and Gynecology (2005) 192: 768-73.
Chopra et al. Radiofrequency ablation of hepatic tumors adjacent to the gallbladder: feasibility and safety. AJR Am J Roentgenol. Mar. 2003;180(3):697-701.
CNN.com Health Women. Experimental technique uses lasers to shrink uterine fibroids. Nov. 28, 2000.
Extended European Search Report in co-pending European Application No. 17870547.1, dated May 21, 2020 in 10 pages.
Hindley, et al. MRI guidance of focused ultrasound therapy of uterine fibroids: Early results. American Journal of Roentgenology, 2004, 183(6): 1173-1719.
International Preliminary Report on Patentability in Application No. PCT/US2017/060674, dated May 14, 2019 in 12 pages.
International Search Report in Application No. PCT/US2017/060674, dated Jan. 12, 2018 in 19 pages.
Kanaoka, et al. Microwave endometrial ablation at a frequency of 2.45 Ghz. A pilot study. J Reprod Med. Jun. 2001; 46(60): 559-63.
Law, et al. Magnetic resonance-guided percutaneous laser ablation of uterine fibroids. J Magn Reson Imaging, Oct. 2000; 12(4):565-70.
Liu, et al. Catheter-Based Intraluminal Sonography. J. Ultrasound Med., 2004, 23:145-160.
Mogami, et al. Usefulness of MR-guided percutaneous cryotherapy. Med. Imaging Technol. 2004, 22(3): 131-6. (English abstract).
MSNBC OnLine Articles, About US: Articles; "Intrauerine Fibroids Can Now Be Treated Nonsurgically" http://www.fibroids.com/news-blog/2004/08/intrauterine-fibroids-can-now-be-treated-nonsurgically/ Aug. 23, 2004.
Okamura, et al. Force Modeling for Needle Insertion into Soft Tissue. IEEE Transactions on Biomedical Engineering, Oct. 2001, 10 (51): 1707-1716.
RSNA 2000 Explore News Release. Lasers Liquefy Uterine Fibroid Tumors. 11:30 a.m. CST, Monday, Nov. 27, 2000.
Senoh, et al. Saline Infusion Contrast Intrauterine Sonographic Assessment of the Endometrium with High-Frequency, Real-Time Miniature Transducer Normal Menstrual Cycle: a Preliminary Report. Human Reproduction, 14 (10): 2600-2603, 1999.
Vascular and Interventional Radiology, SRSC; Nonsurgical Treatment of Uterine Fibroids. Available at http://www.drfibroid.com/treatment.htm. Accessed Apr. 11, 2011.
Websand, Inc., New treatment options for fibroid tumors, Copyright 2002 by WebSand, Inc.
Bao et al., A prototype ultrasound-guided laparoscopic radiofrequency ablation system, Surgical Endoscopy vol. 21, pp. 74-79 (2007), Epub Oct. 5, 2006.
Lumsden et al., Clinical presentation of Uterine Fibroids, Baillieres Clinical Obstetrics & Gynaecology. Jun. 1998;12(2):177-95.
McCreedy et al., Radio Frequency Ablation Registration, Segmentation, and Fusion Tool, Jul. 2006, IEEE transactions on information technology in biomedicine: a publication of the IEEE Engineering in Medicine and Biology Society vol. 10 No. 3, 490-496.

\* cited by examiner

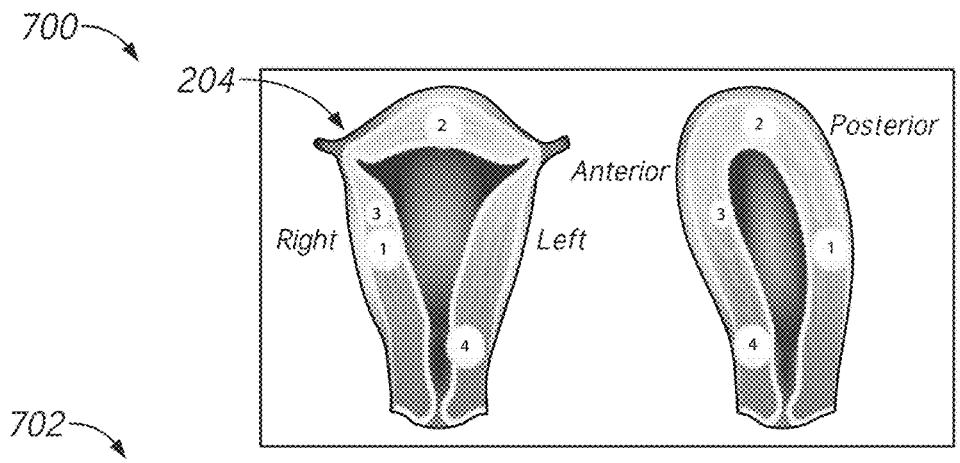

FIG. 7

Fibroid 1

| | |
|---|---|
| Size | Large |
| Location | Body Right Posterior |
| Treated | Treated |
| Angle | 45 |
| Depth | 1.5 |
| Ablation_Size | 1.30 cm |
| Treat_Time | 216 |
| Completed | True |

Fibroid 2

| | |
|---|---|
| Size | Large |
| Location | Fundus Left Anterior |
| Treated | Treated |
| Angle | 60 |
| Depth | 2.7 |
| Ablation_Size | 4.00 cm |
| Treat_Time | 420 |
| Completed | True |

Fibroid 3

| | |
|---|---|
| Size | Large |
| Location | Body Right Anterior |
| Treated | Treated |
| Angle | 45 |
| Depth | 2.4 |
| Ablation_Size | 1.20 cm |
| Treat_Time | 84 |
| Completed | True |

Fibroid 4

| | |
|---|---|
| Size | Large |
| Location | Lower Left Anterior |
| Treated | Treated |
| Angle | 60 |
| Depth | 2.7 |
| Ablation_Size | 2.70 cm |
| Treat_Time | 264 |
| Completed | True |

CONTROLLED TREATMENT OF TISSUE AND DYNAMIC INTERACTION WITH, AND COMPARISON OF, TISSUE AND/OR TREATMENT DATA

INCORPORATION BY REFERENCE

The present application is a continuation of U.S. patent application Ser. No. 17/233,838, filed on May 10, 2019, and issued as U.S. Pat. No. 11,419,682 on Aug. 23, 2022, which is a continuation of U.S. patent application Ser. No. 16/408,790, filed on May 10, 2019, and issued as U.S. Pat. No. 10,993,770 on May 4, 2021, which is a continuation of International Patent Application No. PCT/US2017/060674, filed on Nov. 8, 2017, which claims priority benefit of U.S. Provisional Patent App. No. 62/421,119, filed Nov. 11, 2016. Any and all applications for which a foreign or domestic priority claim is identified in the Application Data Sheet as filed with the present application are hereby incorporated by reference under 37 C.F.R. § 1.57. Additionally, each of U.S. Pat. Nos. 8,088,072 and 8,992,427 is incorporated herein by reference in their entirety so as to form a part of the present application.

TECHNICAL FIELD

The present disclosure relates generally to medical methods and systems for controlling the deployment of needles through the construction of treatment maps. Embodiments of the present disclosure relate to systems and techniques for providing a user interface for dynamic interactions with fibroid data and treatment data. More specifically, embodiments of the present disclosure relate to user interfaces for dynamically providing a visual representation of information generated by aggregating treatment data from one or more medical articles and generating information.

BACKGROUND

Current medical treatments of organs and tissues within a patient's body often use a needle or other elongate body for delivery of energy, therapeutic agents or the like. Some methods use ultrasound imaging to observe and identify a treatment target and predict and track the position of the needle relative to the treatment target.

A treatment for uterine fibroids has recently been proposed which relies on the transvaginal or laparoscopic positioning of a treatment device in the patient's uterus. A radiofrequency or other energy or therapeutic delivery needle is deployed from the device into the fibroid, and energy and/or therapeutic substances are delivered in order to ablate or treat the fibroid. To facilitate locating the fibroids and positioning the needles within the fibroids, the device includes an ultrasonic imaging array with an adjustable field of view in a generally forward or lateral direction relative to an axial shaft which carries the needle. The needle is advanced from the shaft and across the field of view so that the needle can be visualized and directed into the tissue and the targeted fibroid.

SUMMARY

The systems, methods, and devices described herein each have several aspects, no single one of which is solely responsible for its desirable attributes. Without limiting the scope of this disclosure, several non-limiting features will now be described briefly.

Embodiments of the present disclosure relate to an interactive treatment mapping and planning system and techniques for inputting and/or receiving fibroid data, generating information from the fibroid and/or treatment data, and displaying visual representations of the treatment data to enable a user to efficiently obtain information in an interactive user interface. The system may include techniques for providing real-time updates detailing ongoing treatment data. Disclosed herein are systems that advantageously provide highly efficient, intuitive, and rapid dynamic interaction with fibroid data and treatment data to enable the user to generate information about the treatment procedure. The systems may include interactive user interfaces that are dynamically updated to provide rapid comparison of multiple fibroids to be treated. Further, treatment information may be automatically sorted, for example, in some embodiments, by the system according to attributes associated with the treatment procedure and rules and/or preferences of the user.

Systems and methods are disclosed for providing a treatment mapping and planning system. The system provides fibroid location on a user interface. The user interface may comprise a map of the fibroids to be treated and/or treatment procedure information and activity at the individual fibroid level. The user may select a fibroid to be treated from the user interface, and the system may prompt the user to provide the system with information about the fibroid. Accordingly, a user may use the systems described herein to more quickly, thoroughly, and efficiently interact with multiple fibroid information and develop an efficient treatment plan based on the various fibroids to be treated. The features and advantages noted above, as well as others, are discussed in further detail below.

In various embodiments, the system creates a representation of the fibroids to be treated, including for example, descriptions of the fibroids, fibroid locations, fibroid type (e.g., intramural, submucosal, subserosal, pedunculated submucosal, pedunculated subserosal), estimated fibroid sizes, and other fibroid information.

In various embodiments, systems and methods are disclosed for aggregating fibroid and/or treatment data points, and generating information about the treatment procedure. For example, the fibroid and/or treatment data points may comprise at least one of a fibroid location, a fibroid size, a fibroid treatment order, or other fibroid information.

In various embodiments, systems and methods are disclosed for aggregating fibroid and/or treatment data points from various data sources. For example, the various data sources may comprise at least one of an input from a user, a user data source, or a third party data source.

In various embodiments, the system provides color coded icons, including order of treatment and other information. The other information may comprise estimated fibroid size, fibroid treatment status, and other fibroid information. Warnings may alert the user to situations in which a mapped fibroid has not been treated.

In various embodiments, system and methods are disclosed for categorizing the fibroid to be treated based on aggregated fibroid information. The categories may be based on fibroid size, order of treatment, fibroid location, fibroid prior treatment status, and other fibroid information. The system may automatically identify a mapped fibroid as one with particular interest to the user based on the categorization and provide the user with a visual representation indicating the fibroid's status. The user may then select and interact with the fibroid.

In various embodiments, data from the treatment devices may be acquired during the treatment procedure. The treatment data may be automatically and dynamically processed interactively in response to user and treatment device inputs, and the processed data is efficiently and compactly presented to a user by the system. Thus, in some embodiments, the user interfaces described herein are more efficient as compared to previous recording methods in which treatment data is not dynamically updated and compactly and efficiently presented to the user in response to use of the treatment devices.

The system may be configured and/or designed to generate user interface data useable for rendering the various interactive user interfaces described. The user interface data may be used by the system, and/or another computer system, device, and/or software program (for example, a browser program) to render the interactive user interfaces. The interactive user interfaces may be displayed on, for example, electronic displays (including, for example, touch-enabled displays).

In various embodiments, systems and methods are disclosed for generating a user interface including a fibroid map. The fibroid map may include a visual representation of information relating to a fibroid. For example, the visual representation may comprise a fibroid icon.

In various embodiments, systems and methods are disclosed for identifying a fibroid using an imaging modality and generating a user interface configured to provide knowledge relating to the identified fibroid.

In various embodiments, systems and methods are disclosed for acquiring data from an imaging modality. For example the data may comprise at least one of a position of the imaging modality, an orientation of the imagining modality, an insertion depth, an insertion angle, a fibroid location, a fibroid size, or other imagine modality information.

In various embodiments, systems and methods are disclosed for aggregating information about a treatment device via a sensor. For example the information may comprise at least one of a position and orientation of the treatment device.

In various embodiments, systems and methods are disclosed for communicating information from a sensor to a mapping system. For example the sensor may communicate information relating to at least one of a position and orientation of a treatment device.

In various embodiments, systems and methods are disclosed for aggregating information relating to an imaging modality through a tracking system. For example the information may comprise at least one of a position, orientation, and motion of the imaging modality.

Design of computer user interfaces that are useable and easily learned by humans is a non-trivial problem for software developers. The present disclosure describes various embodiments of interactive and dynamic user interfaces that are the result of significant development. This non-trivial development has resulted in the user interfaces described herein which may provide significant cognitive and ergonomic efficiencies and advantages over previous methods. The interactive and dynamic user interfaces include improved human-computer interactions that may provide reduced mental workloads, improved decision-making, reduced work stress, reduced procedure time, increased procedure accuracy, increased procedure documentation, and/or the like, for a user. For example, user interaction with the interactive user interface including interactions with fibroid and/or treatment data, among other interactions described herein may provide optimized interactions in comparison to previous methods.

Various embodiments of the present disclosure provide improvements to various technologies and technological fields. For example, existing treatment mapping and planning application technology is limited in various ways, and various embodiments of the disclosure provide significant improvements over such technology. For example, existing treatment mapping and planning application technology is limited since the treatment data that is provided may not be presented efficiently or at all and interactions between the treatment devices and the system is limited or not provided at all. Various embodiments of the present disclosure are inextricably tied to computer technology. In particular, various embodiments rely on aggregation of fibroid and/or treatment data, generating information about a treatment procedure, displaying such data in interactive graphical user interfaces displayed on electronic displays, etc. In some embodiments, treatment data may include information regarding the treatment device(s), the treatment parameters, the day and/or time of treatment, and other information. Such features are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic data.

Some embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 7 illustrates another example of a treatment report that may be generated by the interactive treatment mapping and planning system in which several fibroids have been treated.

DETAILED DESCRIPTION

Figure 1:
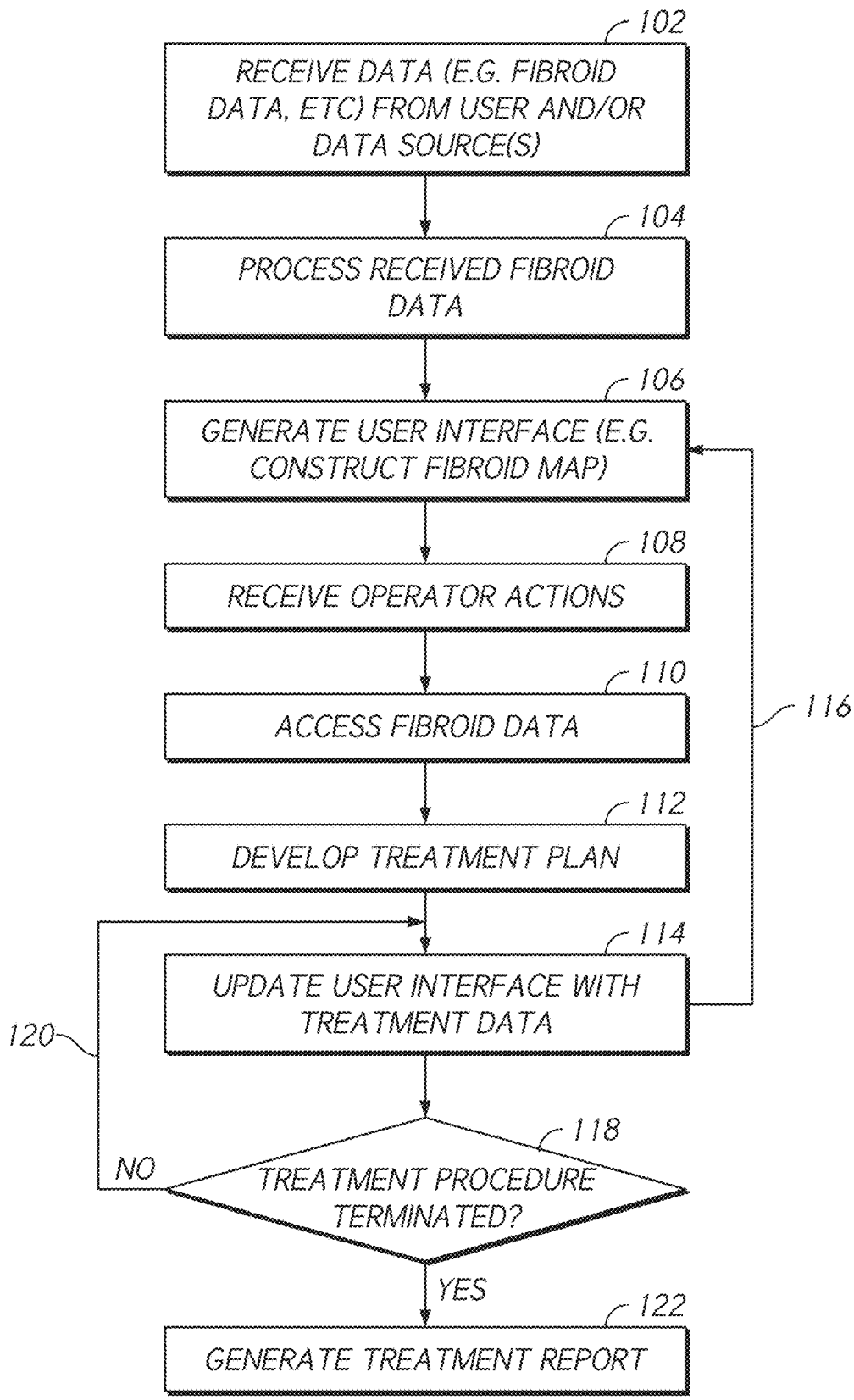
FIG. 1 is a flowchart of an illustrative operation of an example interactive treatment mapping and planning system.

The present disclosure provides improved systems and methods for the treatment of tissues such as uterine fibroids. The systems and methods allow the treating physician to interactively and efficiently access information to assist in the development of a treatment map and plan. Access to such information may facilitate the planning and treatment of targeted tissues and improve the likelihood that proper treatment of a targeted anatomy occurs. The systems and methods provide a user interface for real-time dynamic interactions and feedback regarding treatment data. Such information may allow the physician, if desired, to alter or reassess the treatment plan before and/or during the treatment procedure. The systems and methods provide user interfaces that can dynamically generate a visual representation of information by aggregating treatment data from one or more of the treatment devices and generating useful information.

Feedback or other information is preferably provided visually on a treatment mapping and planning application. The treatment mapping and planning application may generally have graphical user interfaces that include real-time images overlaid by or alongside various objects and fibroid data. In some embodiments, the images may comprise ultrasonic or other imaging screens. An application may further be able to aggregate real-time information gathered from one or more treatment devices and display the information in an interactive manner that provides the user with information. For example, the real-time information may comprise feedback information in response to manipulating the probe and/or activating the needles. The system automatically aggregating the information reduces the need to enter data or commands onto a system controller or display, and can reduce the risk of data being lost altogether.

The application may generate a treatment report including information regarding the fibroid(s), the treatment device, the treatment parameters, the day and/or time of treatment, and other treatment information.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. The structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may be taught or suggested herein.

Unless otherwise noted, the systems and methods described herein may be used with any embodiment described and/or contemplated within U.S. Pat. Nos. 8,088,072 and 8,992,427. It will be understood that any of the embodiments described and/or contemplated within U.S. Pat. Nos. 8,088,072 and 8,992,427 can be modified to be used with the systems and methods described herein.

I. OVERVIEW

An interactive treatment mapping and planning system enables a user to more quickly, thoroughly, and efficiently aggregate fibroid and/or treatment information from a user and/or data source, construct a fibroid map providing a visual representation of the aggregated fibroid information, generate information from the aggregated information about the fibroid to be treated and/or treatment procedure, develop a treatment plan based on the fibroid and/or treatment procedure information, provide real-time information gathered from treatment devices during the treatment procedure, and allow the user to interact with the treatment data. This and other functionality and advantages are provided via interactive graphical user interfaces, including interactive map interfaces, which are inextricably tied to computer technology.

As mentioned above, the system enables a user to efficiently input and/or compile fibroid data, construct a fibroid map, develop a treatment plan, gather information regarding the treatment procedure, and generate a treatment report. The interactive treatment mapping and planning system may include an interactive user interface in which fibroid and/or treatment data may be displayed on a user interface.

Fibroid data may refer to any type of data and/or information related to the fibroid(s) to be mapped. Fibroid data may also be referred to herein as fibroid data items. A fibroid data item generally includes at least a location associated with a fibroid. The location may be specified by, for example in some embodiments, a designated location selected by the user on a projected image located on or alongside a user interface. In some instances, fibroid data may include other information. For example, the fibroid data may comprise a description of the fibroid, fibroid location, fibroid type (e.g., intramural, submucosal, subserosal, pedunculated submucosal, pedunculated subserosal), estimated fibroid size, fibroid prior treatment status, number of fibroids, fibroid treatment order, and/or other fibroid information. Any combination of different types of fibroid data items may be used in the system simultaneously. Fibroid data items may be from various sources, and may be associated with various types of fibroids. Fibroid data may be obtained from a user, a single database, and/or multiple databases. The single and/or multiple databases from which fibroid data may be obtained may be operated, maintained, and/or owned by various entities. For example, the fibroid data may be obtained from a patient database and/or a hospital records management database.

Treatment data may refer to any type of data and/or information related to the treatment procedure. Treatment data may also be referred to herein as treatment data items. A treatment data item generally includes at least information regarding the treatment device(s), the treatment parameters, the day and/or time of treatment, and/or other treatment information. In some instances treatment data may include other information. For example, the treatment data may comprise fibroid treatment order, treatment time, ultrasound device information (such as ultrasound device serial number), ultrasound transducer angle, ultrasound transducer position, ablation device information (such as ablation device serial number), needle deployment depth, electrode deployment length, ablation data, ablation treatment volume, ablation treatment area, ablation time, ablation temperature, electrode and/or tissue impedance, radiofrequency power, radiofrequency temperature, time-temperature graphs, time-radiofrequency power graphs, and/or other treatment information. Any combination of different types of treatment data items may be used in the system simultaneously. Treatment data items may be from various sources. Treatment data may be obtained from a user and/or treatment device(s) throughout a treatment procedure. For example, the treatment data may be obtained from various treatment devices, such as an ultrasound device and/or an ablation device.

FIG. 1 shows a flowchart depicting an illustrative operation of the interactive treatment mapping and planning system. In various embodiments, fewer blocks or additional blocks may be included in the processes, or various blocks may be performed in an order different from that shown in FIG. 1. In an embodiment, one or more blocks in FIG. 1 may be performed by, or implemented in, the interactive treatment mapping and planning system 800 shown in FIG. 8.

At block 102, various fibroid data may be optionally received by the system from a user input and/or one or more databases and/or data sources (including, for example, from databases maintained by the user or third party entities). As an example of the system receiving various fibroid data, the system may access fibroid data from one or more data sources. The data may comprise computer-readable output from a diagnostic test such as a transcervical uterine ultrasound, a laparoscopic ultrasound, or intrauterine ultrasound. The diagnostic test may be performed prior to or contemporaneously with the operation illustrated in FIG. 1.

The data may then optionally be processed by the server at block 104. For example, the fibroid data may be organized by location, type, and/or by any other useful index so as to enable fast searching of the fibroid data.

At block 106, a user interface (and/or user interface data) is generated that displays (and/or is useable to generate and display) a map interface, as described in further detail below. For example, a map interface detailing a constructed fibroid map, as described in further detail below, may be displayed on the user interface. The map interface may be constructed entirely automatically based on the received data, entirely by the user, or a combination thereof. For example, the map interface may auto-populate based on the received data and then be manipulated by the user. In various embodiments, the system creates a visual representation of fibroid data and/or treatment data on the generated user interface, including, for example, descriptions of the fibroids, fibroid locations, fibroid type (e.g., intramural, submucosal, subserosal, pedunculated submucosal, pedunculated subserosal), estimated fibroid sizes, fibroid prior treatment statuses, number of fibroids, fibroid treatment order, and other fibroid information. In various embodiments, the system may create a populated fibroid map following a preliminary exploratory procedure, as described below in reference to FIG. 9.

At block 108, the user may interact with the user interface of the system in any of the ways described below. For example, the user may import additional data, interact with the map interface, provide various search query criteria, etc. At block 110, the fibroid data may be accessed by the system based on the provided user actions. In various embodiments, the treatment system may access one or more internal and/or external databases in response to user actions. The one or more accessed internal and/or external databases may or may not include the fibroid data described above.

At block 112, the system may develop a treatment plan based on the constructed fibroid map. The treatment plan may be developed manually by the user. In some embodiments, the system may develop the treatment plan automatically based on the fibroid data, as described in further detail below. The user may modify an automatically created treatment plan (e.g., changing the treatment order of the fibroids, selecting to skip treatment of some fibroids, etc.). Some changes may be prohibited or generate an error or warning message. The system may suggest changes to a manually created treatment plan.

At block 114, the user interface may be updated in response to the user's actions. The system may update the user interface following initiation of the treatment procedure. The updated interface may include data acquired from a treatment device. For example, the user interface may display information regarding the treatment device(s), the treatment parameters, the day and/or time of treatment, and other treatment information described herein in further detail. Treatment may be prevented by the system unless the treatment can be linked to a specific fibroid. Fibroid information may be displayed in lists and/or in the map interface, and/or animations may be provided, among other interface updates described below. As indicated by arrow 116, the operation may revert to block 108 such that the user may update and/or input a new action. After reversion, one or more of blocks 106, 108, 110, and/or 112 may be skipped.

At block 118, the system determines whether the treatment procedure has been terminated. The system may determine whether sufficient treatment has been performed prior to terminating the treatment procedure. In some embodiments, the system may not terminate the treatment procedure if the system determines that additional treatment is required. As indicated by arrow 120, if the treatment procedure has not terminated, the operation may continue to update the user interface as the user interacts with the system in any of the various ways described here. If the treatment procedure has terminated, the process proceeds to block 122.

In various embodiments, fibroid and/or treatment data may be received and processed by the system at any time and/or continuously. In an embodiment, treatment data may be updated even as the user is viewing the data on the user interface. For example, the user may use the system to analyze substantially real-time treatment data.

At block 122, the system may generate a report following the termination of the treatment procedure. The report may detail treatment information acquired during the treatment procedure. For example, the report may include information regarding the fibroid(s), the treatment device, the treatment parameters, the day and/or time of treatment, etc. The report is described in further detail below.

The system may generate alerts to the user. Alerts may comprise electronic notifications of changes and/or updates, for example, related to a user's actions. For example, as treatment data is updated in the system, the system may determine new or different fibroid classification, or may determine that user interfaces are or would be updated as a result of the updates. Accordingly, in order that the user may be made aware of these changes in a timely manner, an alert and/or notification may be automatically transmitted, for example, to a device operated by the user. The alert and/or notification can be transmitted at the time that the alert and/or notification is generated or at some determined time after generation of the alert and/or notification. When received by the device, the alert and/or notification can cause the device to display the alert and/or notification via the activation of an application on the device. In some embodiments, the device may comprise a browser, a mobile application, etc. For example, receipt of the alert and/or notification may automatically activate an application on the device, such as a messaging application, a standalone application, or a browser, for example, and display information included in the alert and/or notification. In some embodiments, the standalone application may comprise an interactive treatment mapping and planning system application. An alert may include notification that one or more fibroids was not treated, a treatment parameter may be inconsistent with the estimated fibroid size, there was a problem with the treatment device or a portion thereof (e.g., one or more thermocouples providing inconsistent data), etc.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Embodiments of the disclosure may include several novel features, no single one of which is solely responsible for its desirable attributes or which is essential to practicing the embodiments of the disclosure herein described.

II. EXAMPLE USER INTERFACE AND CONSTRUCTING A FIBROID MAP

FIGS. 2-5 illustrate an example of a graphical user interface 200 of the interactive treatment mapping and planning system. The user interface 200 may include an imaging field 202 displaying real-time images obtained from an ultrasound device or another imaging modality. The user interface 200 may further comprise a fibroid map interface 204 to assist a user before and/or during a treatment procedure. The fibroid map interface 204 may allow a user to obtain a comprehensive view of the mapped fibroids and develop a treatment plan prior to initiating a treatment procedure. The fibroid map interface 204 may be created using diagnostic images from an ultrasound device. The fibroid map interface 204 may be based on diagnostic data derived from other systems. The fibroid map interface 204 may display one or more images or illustrations of a uterus. For example, in some embodiments the fibroid map interface 204 may display several views of the uterus. As shown in FIGS. 2-5, the several views may include a uterus front view 206 and/or a uterus side view 208. The one or more uterus views 206, 208 may be annotated with directional indicators (e.g., left, right, lateral, medial, anterior, posterior, dorsal, ventral, inferior, superior) to orient a user interacting with the one or more uterus views 206, 208. For example, a uterus front view 206 may indicate a right side and/or left side. For another example, a uterus side view 208 may indicate an anterior side and/or a posterior side.

The fibroid map interface 204 may be located at various portions of the user interface 200. In some embodiments, the fibroid map interface 204 may overlay a portion of the user interface 200 (e.g., as shown in FIGS. 2-5). The user may interact with the fibroid map interface 204 to resize the fibroid map interface 204 and/or move the fibroid map interface 204 throughout any portion of the user interface 200, for example to change obstruction of the view of the imaging field 202. In some embodiments, the user interface 200 may comprise a separate viewing window or a split-screen window providing the fibroid map interface. In this case, the fibroid map interface 204 will not be displayed obstructing the imaging field 202.

The user interface 200 and/or fibroid map interface 204 may further comprise several additional icons or buttons to increase the system's functionalities. In some embodiments, the user interface 200 may comprise a fibroid map interface view button 210. When a user engages the view button 210, the system may display the fibroid map interface 204. The system may subsequently remove the fibroid map interface 204 from view when the user again engages the view button 210. In some embodiments, the fibroid map interface 204 may be removed from view when a user engages a fibroid map interface close button 212. In some embodiments, the fibroid map interface may be removed from view or reduced in size upon user actions such as operation of a treatment device.

The user interface 200 and/or fibroid map interface 204 may further comprise a treatment report button 214 that, when engaged by the user, causes the system to generate a treatment report 600, 700, discussed in further detail below.

In various embodiments, functionality of the interactive treatment mapping and planning system (as described in reference to the various figures below) may be implemented in one or more software computer modules stored in a memory and executed by one or more hardware processors, as is described below with reference to the example interactive treatment mapping and planning system 800 in FIG. 8. The system 800 can be designed to operate with the treatment device, display the user interface 200, and/or generate the treatment report 600, 700.

In various embodiments, the user interface 200 of FIGS. 2-5 may be displayed on an electronic display viewable by a user of the interactive treatment mapping and planning system. The user of the interactive treatment mapping and planning system may interact with the user interface 200 of FIGS. 2-5 by, for example, touching the display when the display is touch-enabled, using a mouse pointer to click on the various elements of the user interface 200, and/or using a keyboard to input data.

The user of the system may interact with the user interface 200 by scrolling or panning up, down, and/or side to side; zooming in or out; selecting data items; drawing shapes; performing a search queries; and/or the like. Various user actions may reveal more or less user interface 200 and/or fibroid map interface 204 detail, and/or more or fewer data items.

Figure 3:
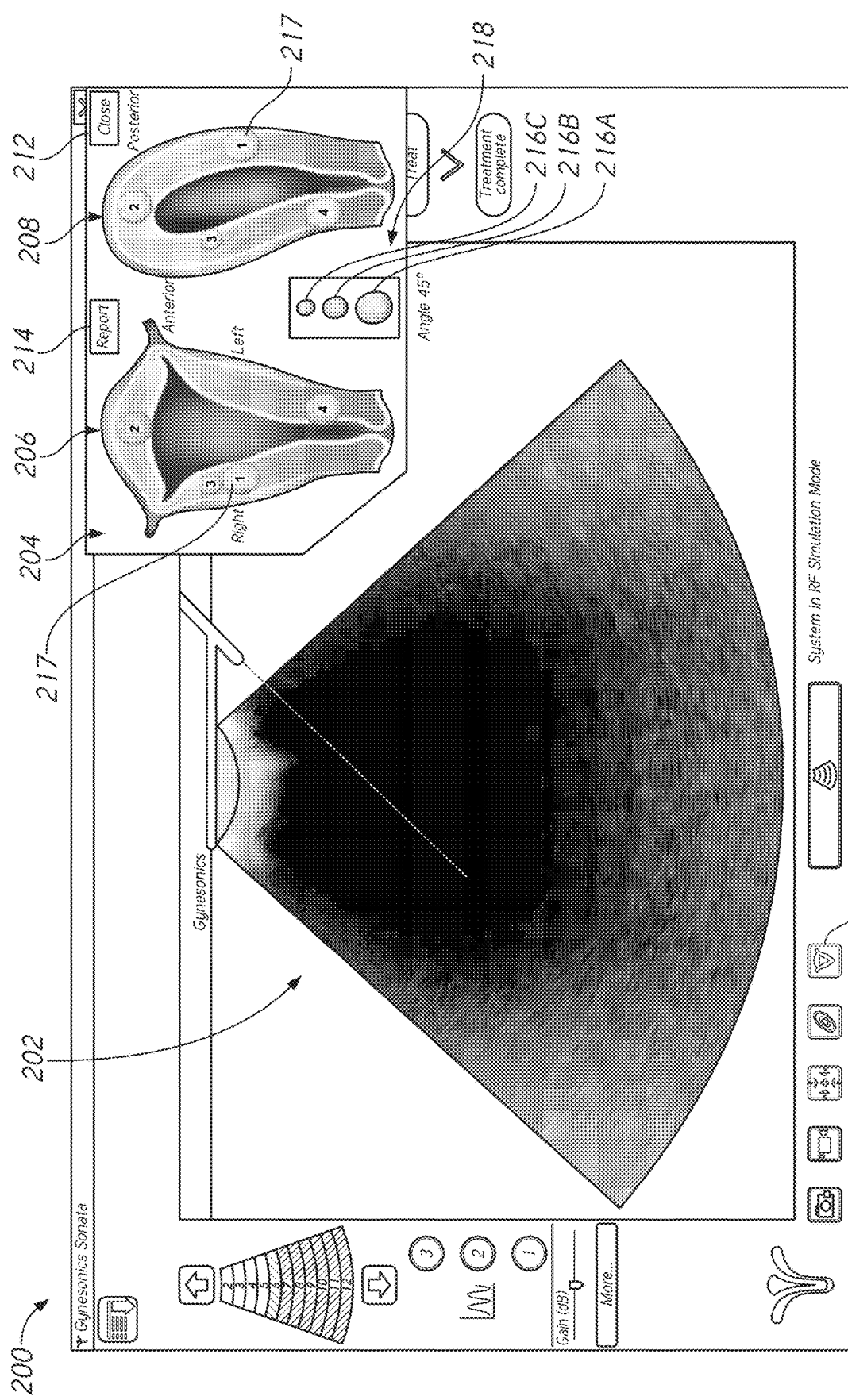
FIG. 3 illustrates an example graphical user interface with a constructed fibroid map located alongside a user interface of the interactive treatment mapping and planning system in which various types of fibroid icons are displayed with a representation of a uterus.

FIG. 3 illustrates an example user interface 200 of the interactive treatment mapping and planning system in which various types of fibroid data items are displayed, according to block 106 of FIG. 1. In some embodiments, the system utilizes the graphical fibroid map interface 204 to display visual representations that provide the user with insightful information about a mapped fibroid. In some embodiments, the system displays a visual representation that provides the user with information relating to fibroid data, among other information, without the user having to go back to the one or more fibroid data source(s).

Prior to initiation of a treatment procedure, the system receives fibroid data. In some embodiments, a user may interact with the user interface 200 and/or fibroid map interface 204 to manually populate the fibroid map interface 204 with fibroid information. The user may review fibroid information based on previously gathered diagnostic results. After locating one or more fibroids through a preliminary ultrasound or other imaging modality exploratory procedure, the user may input the fibroid information into the user interface 200 and/or fibroid map interface 204. The system may automatically populate the fibroid map interface 200 with fibroid information. During the preliminary exploratory procedure, the system may generate fibroid information by aggregating information from a user and/or one or more separate data sources, discussed in further detail below with reference to FIG. 9. In some embodiments, as described above, the system may automatically obtain fibroid data from single and/or multiple databases from which fibroid data may be obtained may be operated, maintained, and/or owned by various entities. The one or more databases may include a patient database and/or a hospital records management database. Following input of the fibroid information, either manually by the user or automatically by the system, the system may track and record the fibroid information.

Various data items, including fibroid data items, may be represented on the fibroid map interface 204 with icons and/or symbols. FIGS. 2-5 illustrate several examples of fibroid icons 216 that may represent fibroid data on the uterus views 206, 208. The user may select and/or otherwise interact with fibroid data for each fibroid icon 216 displayed on the fibroid map interface 204. In various embodiments, the system may display a fibroid icon 216 as a representation of fibroid data, including for example, a description of the fibroid, fibroid location, estimated fibroid size, fibroid prior treatment status, number of fibroids, fibroid treatment order, and other fibroid information.

A user may manually populate the fibroid map interface 204 by interacting with a fibroid icon 216 within a fibroid icon selection tray 218. As discussed above, a user may interact with the system through various means. For example, the user may click and drag a fibroid icon 216 to a desired location. For another example, the user may click a fibroid icon 216 and subsequently click a desired location to place the fibroid icon 216 at the location. The user may click a desired location to place the fibroid icon 216 and subsequently click a fibroid icon 216 to place the fibroid icon 216 at the location. When a user places a fibroid icon 216 in one uterus view 206, 208, the system may automatically populate the other uterus view 206, 208 with a fibroid icon 216 at the same location on the uterus. The user may alter the location of the fibroid icon 216 by interacting with the fibroid icon 216. In some embodiments, when a user moves a fibroid icon 216 up or down in a single uterus view 206, 208, the system may automatically move a corresponding fibroid icon 216 in another uterus view 206, 208. As a user moves a fibroid icon 216 left or right in a single uterus view 206, 208, the system may not alter the location of a corresponding fibroid icon 216 in another uterus view 206, 208. This allows the fibroid icon 216 to maintain the representative horizontal location of the fibroid icon 216 on the fibroid map interface 204.

In various embodiments, the system displays each fibroid icon 216 on the fibroid map interface 204 through a particular visual representation. Each fibroid icon 216 may represent a fibroid type associated with a fibroid data item. The fibroid icon 216 may be chosen from a fibroid icon selection tray 218 based on the properties of the fibroid, as discussed in further detail below. The visual representation may be capable of quickly and efficiently providing the user with valuable fibroid information. The system may assign the particular representation to the fibroid data item based on fibroid information generated from the aggregated information. The visual representations of the fibroid icons 216 may be animated to show, among other things, recent activity, such as a change in fibroid treatment status, fibroid treatment order, or other fibroid information.

The fibroid icon 216 may comprise different sizes to represent variations in the estimated fibroid size. For example, as shown in FIG. 3, the fibroid icon 216 may be selected from a large fibroid icon 216A, medium fibroid icon 216B, and small fibroid icon 216C displayed within the fibroid icon selection tray 218. The fibroid selection tray 218 may comprise a conical or frustoconical scale where a user can click along the longitudinal axis to select from an analog assortment of sizes. The fibroid selection tray 218 may prompt user input of a numerical fibroid estimated size and then base the fibroid icon 216 thereon. A fibroid icon 216 may provide a user with the ability to interact with the fibroid icon 216 to alter the properties of the fibroid icon 216. For example, a user may click and drag on a portion of the fibroid icon 216 to increase or decrease the size of the fibroid icon 216. This provides the user with the option to vary the fibroid icon 216 size to any representative fibroid size desired. Fibroid icons 216 may be circular/spherical (e.g., as shown in FIGS. 2-5) or oblong, elliptical, egg-shaped, or other shapes. In such embodiments, the fibroid icons 216 may be stretched, narrowed, rotated, etc. The user may alter the properties of the fibroid icon 216 prior to and/or after the fibroid icon 216 is placed on the fibroid map interface 204. Fibroid icons 216 may be a graphical representation illustrating the relative fibroid size and fibroid location in a uterus.

Figure 4:
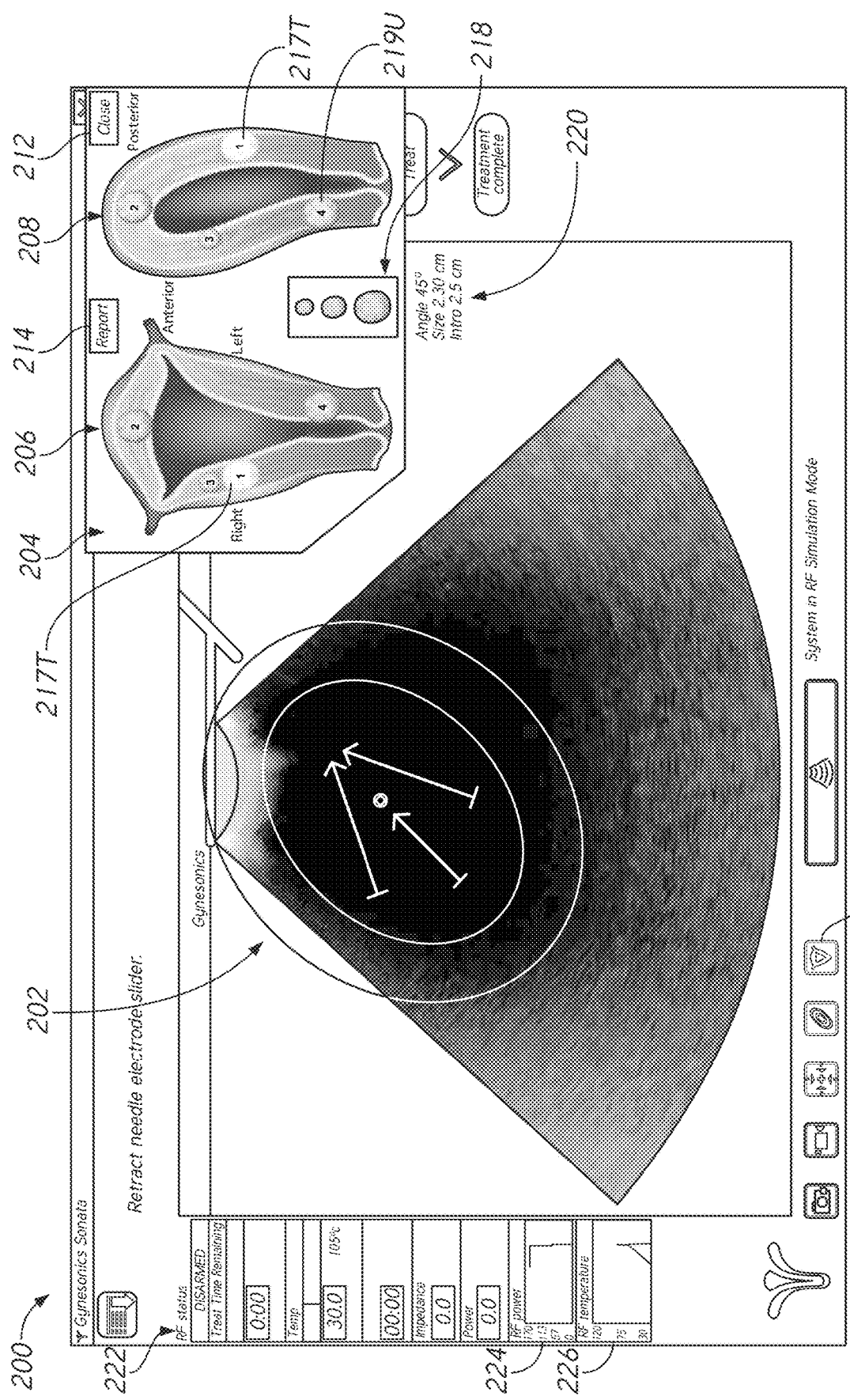
FIG. 4 illustrates an example graphical user interface of the interactive treatment mapping and planning system in which the fibroid map indicates that one fibroid has been treated.
Figure 5:
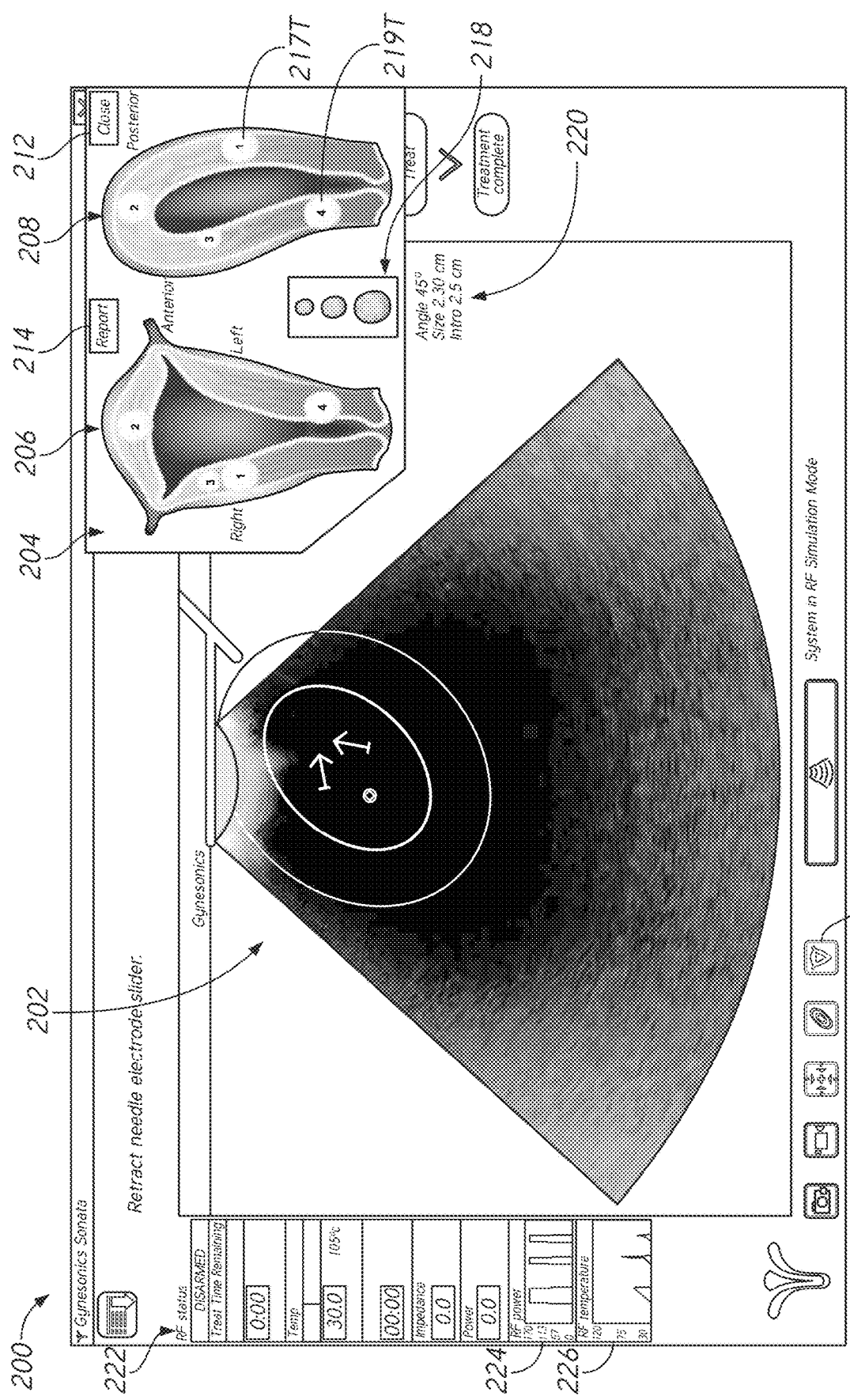
FIG. 5 illustrates an example graphical user interface of the interactive treatment mapping and planning system in which the fibroid map indicates that all fibroids have been treated.

As shown in FIG. 3, a fibroid map interface 204 may display various visual representations that provide the user with insightful information about the mapped fibroid(s). For example, fibroid icon 217 indicates the presence of a large (216A-sized) fibroid located on the posterior side of the right wall of the uterine cavity. The fibroid icon 217 is yellow, which indicates that the fibroid is untreated. As shown in FIGS. 4 and 5, a white fibroid icon indicates that the fibroid has been treated. Other colors and schemes for indication of treatment are also possible. For example, a grey-scale color scheme may be used to differentiate fibroid icons 216 indicating untreated and treated fibroids. The fibroid treatment status may be altered during and/or after a treatment procedure, as described below. FIG. 3 also shows three other fibroids having various estimated sizes and locations.

In some embodiments, the user may select (e.g., by clicking on, hovering over, etc.), via the fibroid map interface 204, one or more of the fibroid icons 216 displayed to cause the system to display additional fibroid details. The additional information may be displayed in the fibroid map interface 204 or in a separate portion of the user interface 200. These capabilities can increase user efficiency by granting the user access to fibroid data through the user interface 200.

In some embodiments, the user may further interact with a fibroid icon 216 to alter various other fibroid properties, such as fibroid treatment order (e.g., if the number indicates order of treatment, changing the number), fibroid treatment status (e.g., marking as treated), fibroid location (e.g., as described above), and/or other fibroid information.

In some embodiments, the user interface 200 and/or fibroid map interface 204 may comprise a legend.

Embodiments of the interactive treatment mapping and planning system relate to systems that facilitate the treatment of a fibroid. It will be understood by one of skill in the art that the fibroids described herein this specification may encompass any fibroid, and are not limited to a particular location or type of fibroid. It is to be understood that the term fibroid is to be broadly construed and encompasses any abnormal tissue growth or any other superficial or other conditions or imperfections within the uterus of the patient or otherwise that benefit from ablation treatment. For example, the term fibroid may be used herein to describe ectopic glandular tissue or myometrial found in the muscular wall of the uterus (adenomyosis or uterine endometriosis).

III. DEVELOPING A TREATMENT PLAN

At block 112 of FIG. 1, the user may develop a treatment plan based on the fibroid map interface 204 following the construction of the fibroid map interface 204. In alternative embodiments, the system may automatically develop a treatment plan based on the constructed fibroid map interface 204 and aggregated fibroid information. The treatment plan may comprise illustrating fibroid icons 216 on the fibroid map interface 204 to include numbering indicating a fibroid treatment order, as shown in FIGS. 3-5. The user and/or system may alter the fibroid treatment order for a fibroid icon 216. An automated fibroid treatment order may be based on one or more parameters including, for example, fibroid size (e.g., largest to smallest, smallest to largest), fibroid location (e.g., most superior to most inferior, most inferior to most superior, most submucosal to most subserosal), likelihood of outgassing, ease of access, combinations thereof, and the like. Parameters may be provided with weighted scores to recommend, as a non-limiting example, treatment of a superior small submucosal fibroid before treatment of an inferior medium intramural fibroid.

The treatment plan may target a fibroid(s) farthest from serosa prior to a fibroid(s) closest to serosa. The treatment plan may target pedunculated submucosal fibroid(s), submucosal fibroid(s), intramural fibroid(s), subserosal fibroid(s), and lastly pedunculated subserosal fibroid(s), in the order recited.

In some embodiments, the fibroid treatment order may be designed to avoid obscuring of the imaging field 202. Obscuring may arise through a process referred to as outgassing that occurs when steam created during ablation of a fibroid alters the quality of images produced by ultrasound or other imaging modalities. As such, a treatment plan may be developed to avoid outgassing. Several factors may affect the extent to which outgassing occurs during the treatment procedure, such as the mapped fibroid location, the fibroid size, other fibroid information, treatment parameters (e.g., temperature, time, temperature ramping, etc.), etc. In some embodiments, a treatment plan may be developed that treats fibroids located farther within a uterine cavity prior to treating fibroids located closer to the cervix. Alternatively, fibroids located closer to the cervix may be treated before fibroids located farther within the uterine cavity. A treatment plan may be developed to treat fibroids located closer to the surface of the uterine lining as opposed to fibroids located deeper within the uterine walls. Fibroid size may be a factor in determining fibroid treatment order. Embodiments of the interactive treatment planning and mapping system may utilize a combinatorial optimization algorithm to determine an improved or optimal fibroid treatment order subject to treatment constraints and/or treatment parameters (e.g., temperature, time, temperature ramping, reducing or avoiding outgassing, fibroid size, fibroid location, number of fibroids, etc.).

In some embodiments, the imaging field 202, the fibroid map interface 204, or a combination of both may be utilized to determine placement and/or location of the treatment device during the treatment procedure. The interactive treatment planning and mapping system may determine placement and/or location of the treatment device based on fibroid data and treatment data. Several factors may affect the placement of the treatment device, such as the mapped fibroid location, the fibroid size, other fibroid information, treatment parameters (e.g., temperature, time, temperature ramping, etc.), and other information. The user interface may further comprise treatment device placement and/or location indications on the imaging field 202, the fibroid map interface 204, or a combination of both. The indications may instruct the user to place the treatment device in a particular position and/or location during the treatment procedure. Embodiments of the interactive treatment planning and mapping system may utilize a combinatorial optimization algorithm to determine an improved or optimal treatment device location and/or placement subject to treatment constraints and/or treatment parameters (e.g., temperature, time, temperature ramping, reducing or avoiding outgassing, fibroid size, fibroid location, number of fibroids, etc.).

The treatment device, in some instances, may be configured to sense its position and/or orientation in space. The treatment device can transmit its position and/or orientation information to the interactive treatment planning and mapping system. The system may incorporate the position and/or orientation information into the imaging field 202, the fibroid map interface 204, or a combination of both to be displayed to a user. The treatment device may include one or more sensors to measure the position and/or orientation in three-dimensional space of the treatment device. The sensors may communicate the position and/or orientation information to the interactive treatment planning and mapping system, such that a position and/or orientation information of the treatment device can be displayed in the imaging field 202 and/or fibroid map interface 204. In some instances, the treatment device is in the form of an ablation tool comprising a needle, but the treatment device can include other ablation and/or imaging devices, or may only include an imaging device (e.g., for diagnostic uses).

In some embodiments, the treatment device comprises one or more sensors configured to measure an insertion depth of the treatment device during a treatment procedure. The insertion depth can be communicated to the interactive treatment planning and mapping system such that depth of the treatment device can be displayed in the imaging field 202, the fibroid map interface 204, or a combination of both. In some instances, the treatment device is configured to measure an insertion angle of the treatment device during a treatment procedure. The insertion angle information may be transmitted to the interactive treatment planning and mapping system to be displayed in the imaging field 202, the fibroid map interface 204, or a combination of both.

In some embodiments, the treatment device may include one or more sensors configured to determine a device position and/or orientation relative to other objects, such as, for example, a fibroid location, a user, one or more locations on a patient, combinations thereof, and the like. Information corresponding to the sensed position and/or orientation is transmitted to the interactive treatment planning and mapping system. Position and/or orientation information between the treatment device and a fibroid to be ablated may be captured by an external tracking system, such as, by way of non-limiting example, an optical tracking system. The tracking system can be configured to obtain at least one of position, orientation, and motion information of the treatment device used. The information sensed by the tracking system can be transmitted to the interactive treatment planning and mapping system. The system may be configured to receive the information and to display it in the imaging field 202, the fibroid map interface 204, or a combination of both. The position and/or orientation information may be determined by any suitable approaches to measure and determine the position and orientation of an object in three-dimensional space. For example, an optical tracking system and/or inertial sensors (for example, gyroscope sensors and/or accelerometers) can be configured to obtain one or more of position, orientation, and motion information of the treatment device. In some instances, the treatment device may include visual markers that provide placement and/or location indications to a user. For example, the treatment device may be annotated with positional indicators (e.g., depth indications) along at least a portion of the treatment device to orient a user interacting with the treatment device. Indicators may be active (e.g., light-emitting diodes) and/or passive (e.g., optically recognizable patterns).

In some implementations, the treatment device may comprise an alignment system that periodically emits a signal which is may be captured by one or more corresponding receivers. In some embodiments, the one or more receivers may sense the signal from the treatment device directly. The alignment system may comprise a source of electromagnetic radiation and emit a signal comprising electromagnetic radiation. For example, the source may be configured to transmit a signal that is capable of traveling through one or more portions of a patient anatomy to be received by a corresponding receiver located outside of a patient cavity.

The position and/or orientation information transmitted to the interactive treatment planning and mapping system may be used in conjunction with fibroid data so that the locations of the treatment device in the imaging field 202 and/or the fibroid map interface 204 correspond to an actual location of the treatment device relative to one or more fibroids. The ability to obtain position and/or orientation data of the treatment device as the user is performing a treatment or diagnostic procedure can help the user perform a fibroid treatment at an optimal location. For example, during a treatment procedure, the interactive treatment planning and mapping system may instruct a user via the imaging field 202 and/or fibroid map interface 204 to guide the treatment device to an appropriate depth, position, and/or orientation for a therapeutic procedure. In some instances, the movement of the treatment device can be projected on the imaging field 202 and/or fibroid map interface 204 in real-time during the treatment procedure. For example, as the treatment device is moved through a patient cavity, the location of a distal tip of the treatment device can be identified on the imaging field 202 and/or fibroid map interface 204. When the treatment device is positioned in a target location within the patient cavity, the treatment device may be positioned in the target location in the imaging field 202 and/or fibroid map interface 204.

IV. Updating A User Interface with Treatment Data

At block 114 shown in FIG. 1, the user interface 200 may be updated before and/or during a treatment procedure in response to the user's actions. In some embodiments, the system may update the user interface 200 following initiation of the treatment procedure. The updated user interface 200 may include data acquired from the treatment devices, such as an ultrasound device and an ablation device. For example, as discussed above, the user interface 200 may display information regarding the treatment device(s), the treatment parameters, the day and/or time of treatment, and other treatment information described herein in further detail. In some embodiments, as shown in FIGS. 4-5, the fibroid map interface 204 may be updated to include treatment parameters 220. The displayed treatment parameters may comprise an ultrasound transducer angle relative to needle longitudinal axis ("Angle"), an ablation diameter along the minor axis ("Size"), needle deployment depth ("Intro"), electrode deployment length, and/or other treatment data.

The user interface 200 may further comprise a treatment data interface 222 detailing the elapsed treatment time, treatment time remaining, ablation treatment volume, ablation treatment area, ablation time, ablation temperature, electrode and/or tissue impedance, radiofrequency power, radiofrequency temperature, and/or any other desired treatment data. In some embodiments, the treatment data interface 222 may comprise a power graph 224 illustrating the relationship between time and radiofrequency power. The treatment data interface 222 may comprises a temperature graph 226 illustrating the relationship between time and mapped fibroid temperature.

In various embodiments, fibroid and/or treatment data may be received and processed by the system at any time and/or continuously. As indicated by block 118 in FIG. 1, the system may determine whether the treatment procedure has been terminated. In some embodiments, termination can be determined by the user clicking the treatment report button 214 or the completed treatment of all mapped fibroids. If the treatment procedure has not been terminated, the system may continuously update the user interface 200 as the treatment procedure continues, as shown by arrow 120. In an embodiment, treatment data may be updated even as the user is viewing the data on the user interface 200. For example, the user may use the system to analyze substantially real-time treatment data through the treatment interface 222 and/or fibroid map interface 204.

In various embodiments, the system may provide color coded representations. For example, the system may characterize a fibroid icon 216 into various classifications such as treatment status classifications: untreated, treated, previously treated but recurring fibroid, or untreated with a previous failed treatment attempt. The individual classifications may result in variations in the visual representation of the fibroid icon 216. For example, as shown in FIG. 4, color coded representation of fibroid icon 217T may indicate a treated fibroid, while fibroid icon 219U may represent an untreated fibroid. The user may interact with a fibroid classification before, during, and/or after a treatment procedure. In some embodiments, a user may manually change a fibroid icon 216 to modify the treatment status of a fibroid icon 216 from "untreated" to "treated" after treating the fibroid. Alternatively, the system may automatically modify the fibroid icon's 216 treatment status based on treatment data received from the treatment device(s). The change in treatment status may automatically alter the visual representation of the fibroid icon 216 to properly indicate the updated fibroid treatment status. In some embodiments, the classification of an untreated fibroid may initiate a warning or alert to the user relating to the fibroid. If a fibroid is treated for a second time, for example because a first treatment was not able to capture the entire fibroid or the portion of the fibroid to be treated, the fibroid icon 216 may change to a third color, have a treatment quantity indicator (e.g., "2"), combinations thereof, and the like.

V. Example Treatment Report

Figure 6:
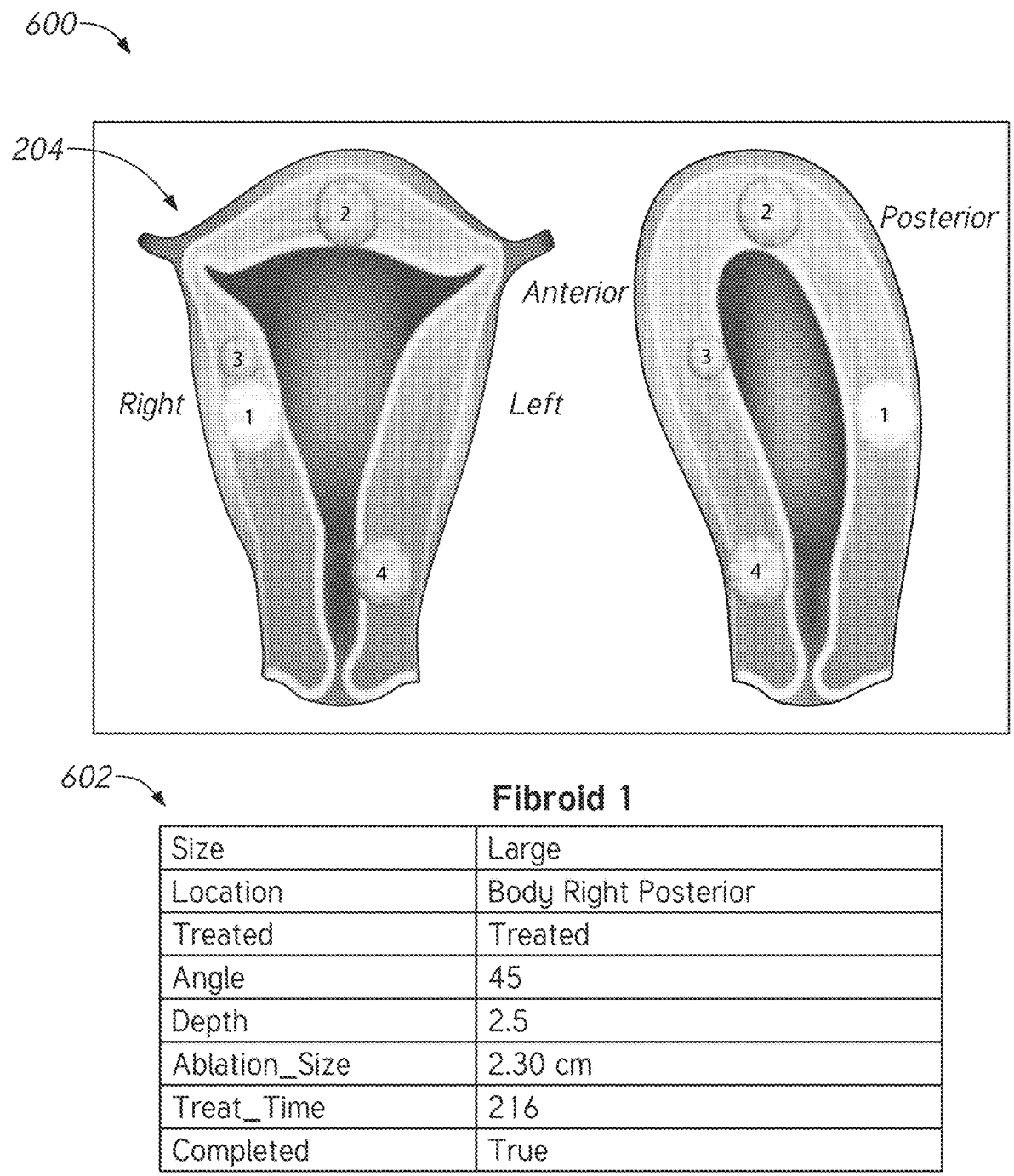
FIG. 6 illustrates an example of a treatment report that may be generated by the interactive treatment mapping and planning system in which a single fibroid has been treated.

As discussed previously, at block 122 in FIG. 1, the system may automatically generate a treatment report 600, 700 following the termination of the treatment procedure, as shown in FIGS. 6-7. A user may interact with the treatment report button 214 to instruct the system to generate a treatment report 600. For example, the report 600 of FIG. 6 may be generated by a user clicking the treatment report button 214 after treating the fibroid 217T at the time of FIG. 4, and the report 700 of FIG. 7 may be generated by a user clicking the treatment report button 214 after treating all of the fibroids at the time of FIG. 5.

The treatment report 600, 700 may detail treatment information acquired during the treatment procedure. For example, the treatment report 600, 700 may include information relating to fibroid location, estimated fibroid size, fibroid treated status, number of fibroids, fibroid treatment order, ultrasound device information (such as ultrasound device serial number), ultrasound transducer angle, ablation device information (such as ablation device serial number), needle deployment depth, electrode deployment length, planned fibroid size, ablation data, ablation data, ablation treatment volume, ablation treatment area, ablation time, ablation temperature, electrode and/or tissue impedance, radiofrequency power, radiofrequency temperature, time-temperature graphs, time-radiofrequency power graphs, ablation safety zone distance, photographs and/or screen shoots of the imaging field, treatment procedure information, time of treatment, treatment length, treatment date, patient data, attending physician and/or nurse, user and/or physician notes, and other fibroid and/or treatment information.

FIG. 6 illustrates an example treatment report 600. In some embodiments, the treatment report 600 may include the fibroid map interface 204 along with an individual fibroid report 602. For example, as shown in FIG. 6, the treatment procedure may have been limited to a single fibroid. In this instance, the treatment report 600 may include only one fibroid report 602. The report may include information about all mapped fibroids, only treated fibroids (e.g., as shown in FIG. 6), or a subset of selected fibroids. The report may include a warning flag related to a fibroid (e.g., red text indicating a treatment time not commensurate with an estimated size). The treatment report 700 may include multiple fibroid reports 702, as shown in FIG. 7.

In some embodiments, the treatment report 600, 700 and/or fibroid report(s) 602, 702 may be exported to one or more databases. The system may export the report 600, 700 through wired and/or wireless connections.

VI. Exploratory Procedure

The interactive treatment mapping and planning system may incorporate a preliminary exploratory procedure. The system may enable a user to more efficiently aggregate fibroid information during an exploratory procedure, construct a fibroid map providing a visual representation of the aggregated fibroid information, and generate an exploratory report.

Figure 8:
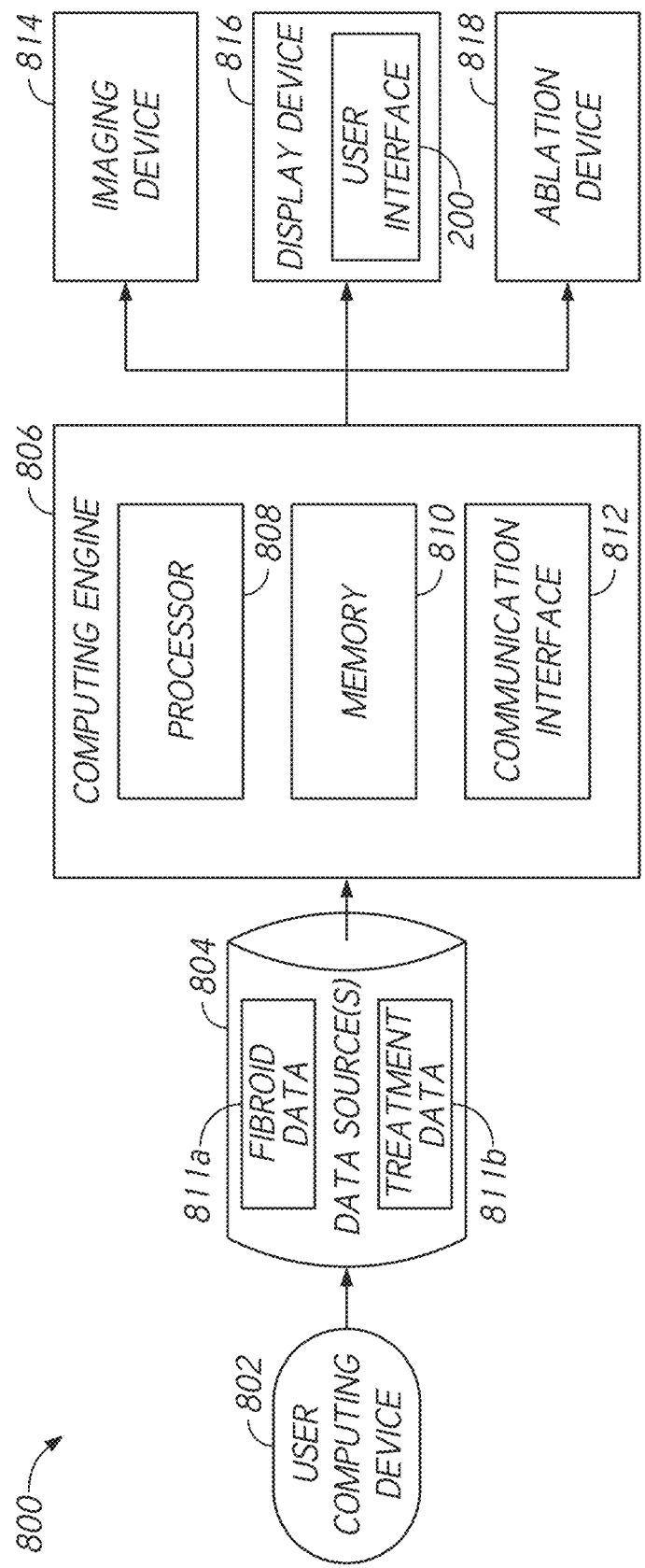
FIG. 8 is a block diagram that illustrates an example interactive treatment mapping and planning system.
Figure 9:
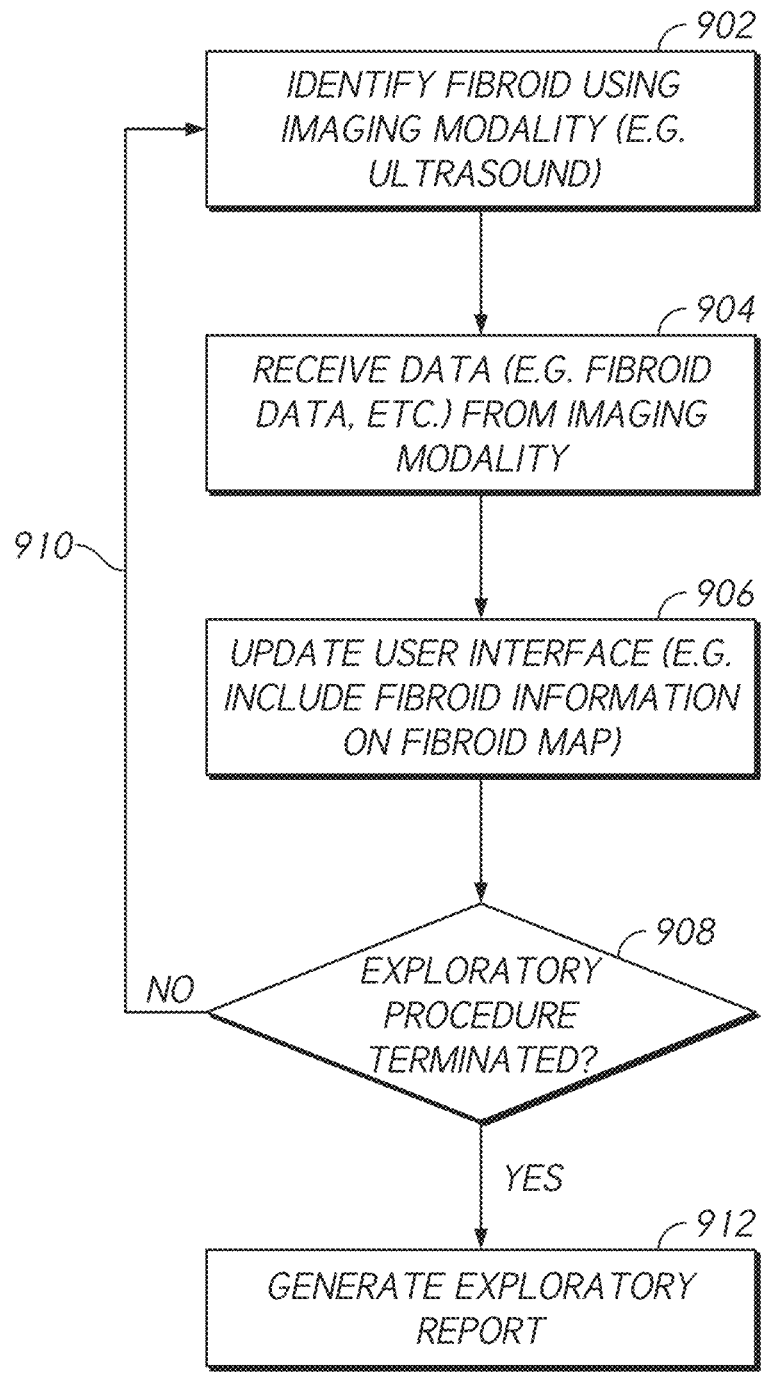
FIG. 9 is a flowchart of an illustrative operation of an example interactive treatment mapping and planning system.

FIG. 9 shows a flowchart depicting an illustrative operation of the preliminary exploratory procedure. In various embodiments, fewer blocks or additional blocks may be included in the processes, or various blocks may be performed in an order different from that shown in FIG. 9. In an embodiment, one or more blocks in FIG. 9 may be performed by, or implemented in, the interactive treatment mapping and planning system 800 shown in FIG. 8.

At block 902, various fibroid data may be identified during a preliminary exploratory procedure performed via a diagnostic test such as a transcervical uterine ultrasound, laparoscopic ultrasound, or intrauterine ultrasound. The system may receive the fibroid data from the imaging device(s) at block 904.

In some instances, at block 902, diagnostic device placement and/or location data may be identified during a preliminary exploratory procedure. The interactive treatment mapping and planning system may utilize any structure, device, method, or features described herein in relation to the treatment device. For example, the diagnostic device may include one or more sensors to measure the position and orientation in three-dimensional space of the diagnostic device. The diagnostic device can transmit its position and/or orientation information to the interactive treatment planning and mapping system. The system may incorporate the position and orientation information into a user interface to be displayed to a user. The method may end after such automated mapping.

At block 906, a user interface is generated that displays (and/or is useable to generate and display) a fibroid map interface similar to the user interface and fibroid map interface previously described above with reference to FIGS. 2-5. The fibroid map interface may be constructed entirely automatically based on the received data, entirely by the user, or a combination thereof. For example, the map interface may auto-populate based on the received data and then be manipulated by the user. In various embodiments, the system creates a visual representation of fibroid data on the generated user interface, including, for example, descriptions of the fibroids, fibroid locations, fibroid type (e.g., intramural, submucosal, subserosal, pedunculated submucosal, pedunculated subserosal), estimated fibroid sizes, fibroid prior treatment statuses, number of fibroids, fibroid treatment order, and other fibroid information. In some embodiments, the system creates a visual representation of diagnostic device data on the generated user interface, including, for example, a position, orientation, motion, and/or other device information.

Figure 10A:
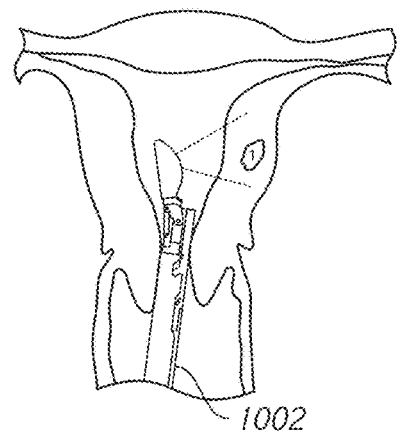
FIG. 10A is an example diagnostic device of the interactive treatment mapping and planning system configured to identify fibroids within a uterus.
Figure 10B:
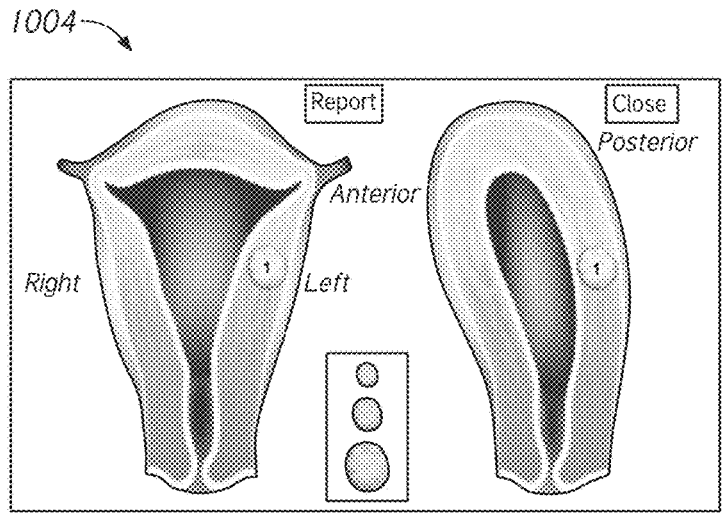
FIG. 10B illustrates an example of a fibroid map interface of the interactive treatment mapping and planning system in which various types of fibroid icons can be displayed with a representation of a uterus.
Figure 10C:
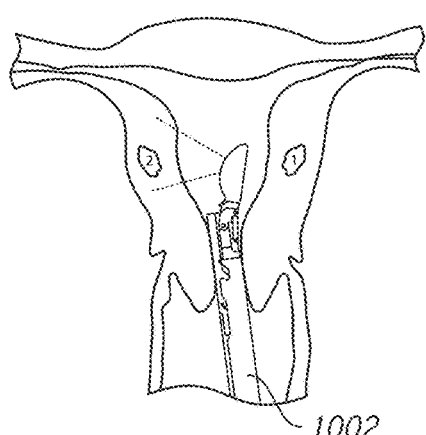
FIG. 10C is an example diagnostic device of the interactive treatment mapping and planning system configured to identify fibroids within a uterus.
Figure 10D:
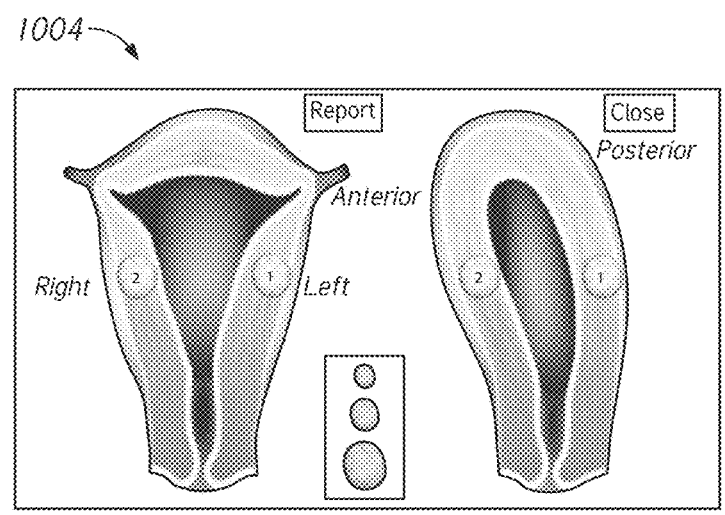
FIG. 10D illustrates an example of a fibroid map interface of the interactive treatment mapping and planning system in which various types of fibroid icons can be displayed with a representation of a uterus.

FIGS. 10A-10D illustrate an example of a diagnostic device 1002 and a fibroid map interface 1004. The fibroid map interface 1004 may utilize any structure, device, method, or features described herein in relation to the interactive treatment mapping and planning system. In some instances, the system may receive fibroid data from the diagnostic device 1002 to auto-populate the fibroid map interface 1004 with fibroid information. Through an exploratory procedure, the diagnostic device 1002 may transmit fibroid information (e.g., fibroid location) to the system to input into the fibroid map interface 1004. Transmission of fibroid information may be based at least partially on sensor data (e.g., providing position and/or orientation information), for example in accordance with certain devices described herein. After locating a first fibroid, the system may automatically populate the fibroid map interface 1004 with the fibroid information. For example, as illustrated in FIGS. 10A and 10B, the diagnostic device 1002 may identify fibroid 1 and transmit fibroid information to allow the system to display a fibroid icon 1 on the fibroid map interface 1004. In some embodiments, the diagnostic device 1002 may identify a plurality of fibroids and transmit a plurality of fibroid information to be displayed on the fibroid map interface 1004. FIGS. 10C and 10D illustrate that, in some instances, the diagnostic device 1002 may identify fibroid 2 and transmit fibroid information to allow the system to display a fibroid icon 2 on the fibroid map interface 1004. As described herein, the system may generate fibroid information by aggregating information from the diagnostic device.

At block 908, the system determines whether the exploratory procedure has terminated. As indicated by arrow 910, if the exploratory procedure has not terminated, the operation may continue to identify additional fibroid(s). For example, with reference to FIG. 3, the fibroid icon 217 may be generated on a first pass of blocks 902, 904, 906, 908, and then a second icon may be generated on a second pass blocks 902, 904, 906, 908, etc. At each block 906, fibroid icons from that pass and previous passes may be updated. If the exploratory procedure has terminated, the process proceeds to block 912.

At block 912, the system may automatically generate an exploratory report following the termination of the exploratory procedure. The report may detail exploratory information acquired during the exploratory procedure. For example, the report may include information regarding the fibroid(s), the imaging device (e.g. an ultrasound transducer), the imaging parameters, the day and/or time of exploratory procedure, and other information. The exploratory report may include an automated and/or manual treatment protocol recommendation (e.g., labeling fibroid icons based on a recommended treatment order rather than the order in which the fibroids were diagnosed).

In various embodiments, the system may export a fibroid data file comprising the constructed fibroid map interface and/or exploratory report. The exploratory report may be readable to automatically populate a fibroid interface map 204.

VII. Implementation Mechanisms

FIG. 8 is a block diagram that illustrates an example of an interactive treatment mapping and planning system 800 that can implement the various methods and functionality described herein (e.g., the operation methods described with reference to FIGS. 1 and 9 and the user interfaces 200 described with reference to FIGS. 2-5, and the reports 600, 700 described with reference to FIGS. 6 and 7).

Figure 2:
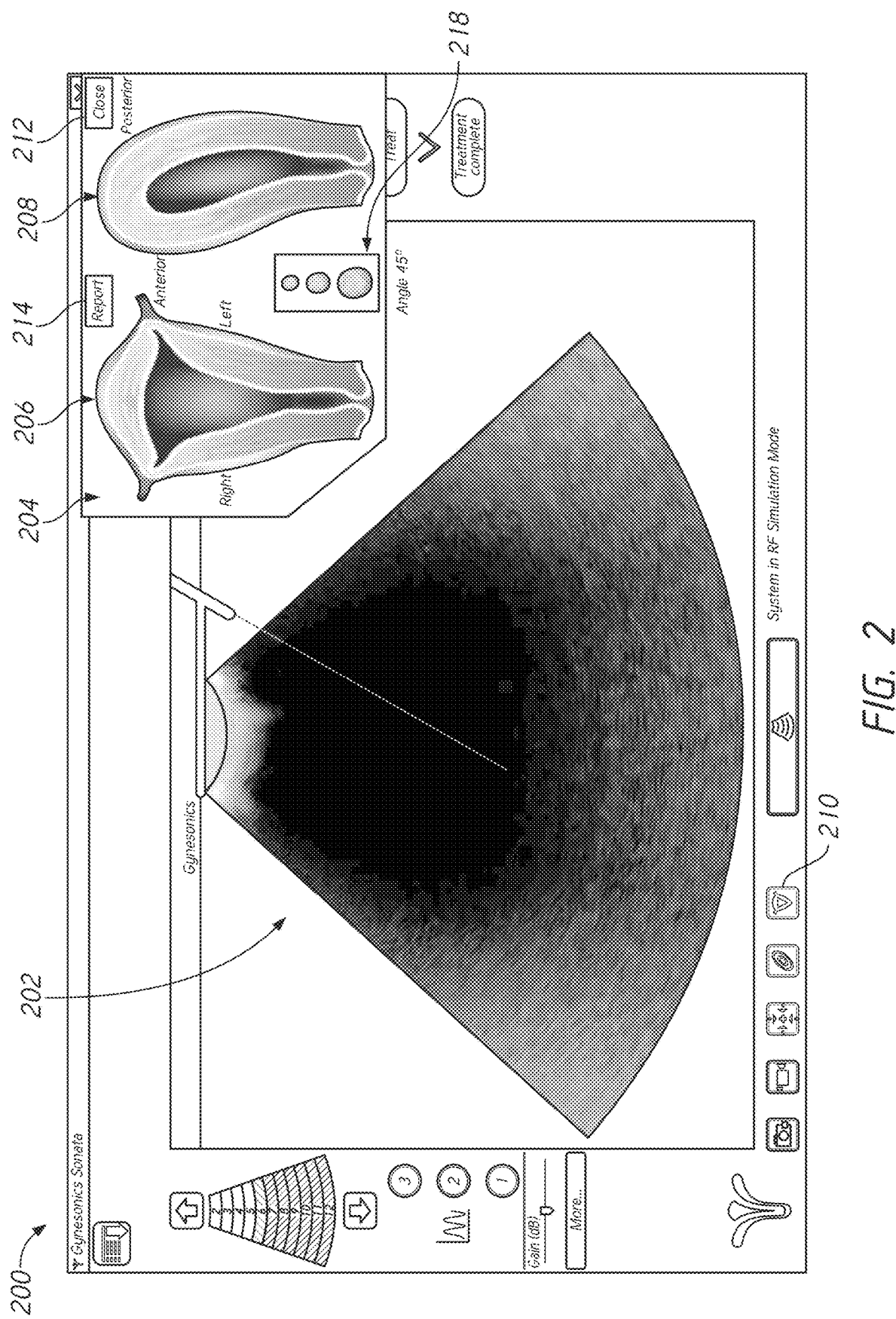
FIG. 2 illustrates an example graphical user interface of an interactive treatment mapping and planning system.

As previously discussed, the interactive treatment mapping and planning system 800 may comprise an imaging device 814 (e.g. an ultrasound transducer or other imaging modality), a display device 816, and an ablation device 818 configured to generate radiofrequency energy for the treatment of an abnormal tissue growth. The treatment system 800 may comprise any embodiment described and/or contemplated within U.S. Pat. No. 8,088,072 (herein referred to as the '072 Patent) and U.S. Pat. No. 8,992,427 (herein referred to as the '427 Patent), incorporated herein by reference in their entireties. It will be understood that any of the embodiments described and/or contemplated within the '072 Patent and the '427 Patent can be modified to be used with the various interactive treatment mapping and planning systems described herein. For example, in some embodiments, FIGS. 1 and 2 of the '427 Patent depict the treatment system 800 illustrated in FIG. 8 of the present application. In some embodiments, the treatment system 800 may comprise treatment probe 16, the imaging device 814 may comprise imaging component 28, and the ablation device 818 may comprise needle component 26, as shown in FIG. 2 of the '427 Patent.

The interactive treatment mapping and planning system 800 can include a computing engine 806, a data source 804, an imaging device 814, a display device 816, and an ablation device 818. The system 800 can receive user (e.g., physician) input from one or more user computing devices 802. In an embodiment, the computing device(s) 802 may be any computing devices capable of displaying software applications to a user and receiving input from the user. For example, the computing device(s) 802 may include smartphones, tablets, laptops, and/or other types of computing devices. The computing device(s) 852 may be capable of communicating over a network, for example, to request data from, and/or to provide data to, the components of the system 800. In some embodiments, the data source 804 may include non-transitory computer-readable medium storage for storing fibroid data 811a and/or treatment data 811b.

The computing engine 806 may perform a variety of tasks to implement the operations of the interactive treatment mapping and planning system. The computing engine 806 can include a hardware processor 808, a memory 810 (which can store code modules executed by the processor 808), and a communication interface 812 that communicates information to and/or from other components of the system 800.

The computing engine 806 may include one or more software modules stored in the memory 810 and that, when executed by the processor 808, may, for example, receive fibroid data 811a and/or treatment data 811b from the data source 804, process the received data, generate user interfaces 200 and/or user interface data for display by the display device 816, process inputs from the user received from the computing device 802 or via the user interface (UI) 200 of the display device 816, and/or update the user interface 200. The processor 808 may be programmed to perform embodiments of the methods described with reference to FIGS. 1 and 9.

The computing engine 806 may be in communication with the data source 804. The database 804 may include electronic storage local to the computing engine 806. The data source 804 may be embodied in hard disk drives, solid state memories, and/or any other type of non-transitory, computer-readable storage medium remotely or locally accessible to the computing engine 806. The fibroid data 811*a* and/or the treatment data 811*b* may be distributed or partitioned across multiple storage devices, and/or may be combined into a single database.

In various embodiments, the computing engine 806 or data source 804 may be accessible by the user through a web-based viewer, such as a web browser, executed by the user computing device 802 or displayed as the display device 816. The display device 816 may be a computer monitor, a touchscreen, an electronic (e.g., LCD or LED) display, etc. The user interface may be generated by the computing engine 806 and transmitted to the web browser of the user computing device 802 or the display device 816. Alternatively, data necessary for generating the user interface 200 may be provided by the computing engine 806 to the display device 816, where the user interface may be generated for display. The user may interact with the user interface 200 through the web-browser or the display device 816. In an embodiment, the user interface 200 of the interactive treatment mapping and planning system 800 may be accessible through a dedicated software application (rather than a web browser).

The interactive treatment mapping and planning system 800 and other methods and techniques described herein can be implemented by one or more special-purpose computing devices such as the processor 808 and the memory 810. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors specially programmed to perform the techniques pursuant to program instructions in firmware, in executable code modules stored in the memory 810, other storage, or a combination. Such special-purpose computing devices may combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or specialized program logic to implement the techniques described herein. Execution of the sequences of instructions contained in the memory 806 causes the processor(s) 804 to perform the process steps described herein.

VIII. Examples

1. A system comprising:
   a non-transitory computer readable storage medium configured to store program instructions; and
   a processor programmed to execute the program instructions to cause the processor to:
   aggregate, from one or more data sources, a plurality of fibroid data records;
   extract, from the plurality of fibroid data records, fibroid data record items; and
   generate user interface data for rendering an interactive user interface on an electronic display, the interactive user interface including:
   an interactive fibroid map, and
   a visual representation of a fibroid data record item, the visual representation comprising a marker on the interactive fibroid map at a respective fibroid location associated with the fibroid data item, the visual representation configured to provide information relating to the fibroid data record item.

2. The system of Example 1, wherein the processor is programmed to aggregate a plurality of fibroid data records from at least one of:
   an input from a user;
   a user data source; or
   a third party data source.

3. The system of any one of Examples 1-2, wherein the fibroid data record item comprises a fibroid location.

4. The system of any one of Examples 1-3, wherein the fibroid data record item comprises a fibroid size.

5. The system of Example 4, wherein the fibroid size comprises one of:
   small;
   medium; or
   large.

6. The system of any one of Examples 1-5, wherein the fibroid data record item comprises a fibroid treatment status.

7. The system of any one of Examples 1-6, wherein the fibroid data record item comprises a fibroid treatment order.

8. The system of any one of Examples 1-7, wherein the processor is further programmed to receive user input.

9. The system of Example 8, wherein the user input comprises at least one of:
   user fibroid data record items; or
   treatment data record items.

10. The system of Example 9, wherein the processor is programmed, in response to the user input, to:
    update the one or more data sources with the user fibroid data record item; and
    update the user interface data such that the interactive user interface includes an indication of at least one of the user fibroid data record items.

11. The system of any one of Examples 8-10, wherein the user input includes export criteria comprising at least one of:
    an export content;
    an export format; or
    an export location.

12. The system of Example 11, wherein the processor is programmed, in response to the user input, to:
    extract, from the fibroid data records, fibroid data export items relating to the export content;
    generate an export document comprising the export format and the fibroid data export items;
    store the export document at the export location; and
    update the user interface data such that the interactive user interface includes an indication of the export request.

13. The system of any one of Examples 1-12, wherein the interactive user interface further comprises a legend.

14. The system of any one of Examples 1-13, wherein the visual representation comprises a fibroid icon.

15. The system of Example 14, wherein the visual representation is configured to indicate a warning to the user.

16. The system of any one of Examples 1-15, wherein the processor is programmed to:
    identify a fibroid using a information from an imaging modality;
    receive fibroid data from the imaging modality; and
    generate an exploratory report.

17. The system of any one of Examples 1-16, wherein the processor is programmed to:
    receive fibroid data from a one or more data sources;
    generate user interface data for rendering an interactive user interface on an electronic display, the interactive user interface including:

an interactive fibroid map, and a visual representation of a fibroid data record item, the visual representation comprising a marker on the interactive fibroid map at a respective fibroid location associated with the fibroid data item, the visual representation configured to provide information relating to the fibroid data record item;

receive treatment data from a treatment device; and update the user interface with treatment data.

18. The system of Example 17, wherein the program further programmed to generate a treatment report.

19. A system comprising:

a non-transitory computer readable storage medium configured to store program instructions; and a processor programmed to execute the program instructions to cause the processor to:

identify a fibroid using a information from an imaging modality;

receive fibroid data from the imaging modality; and generate a user interface data for rendering an interactive user interface on an electronic display, the interactive user interface including:

an interactive fibroid map, and a visual representation of a fibroid data record item, the visual representation comprising a marker on the interactive fibroid map at a respective fibroid location associated with the fibroid data item, the visual representation configured to provide information relating to the fibroid data record item.

20. The system of Example 19, further comprising the imaging modality, wherein the imaging modality comprises an ultrasound transducer.

21. The system of any one of Examples 19-20, wherein the program instructions further cause the processor to generate an exploratory report.

22. A system comprising:

a non-transitory computer readable storage medium configured to store program instructions; and a processor programmed to execute the program instructions to cause the processor to:

receive fibroid data from a one or more data sources;

generate user interface data for rendering an interactive user interface on an electronic display, the interactive user interface including:

an interactive fibroid map, and a visual representation of a fibroid data record item, the visual representation comprising a marker on the interactive fibroid map at a respective fibroid location associated with the fibroid data item, the visual representation configured to provide information relating to the fibroid data record item;

receive treatment data from a treatment device; and update the user interface with treatment data.

23. The system of Example 22, wherein the program further programmed to generate a treatment report.

24. The system of any one of Examples 22-23, further comprising an imaging modality, wherein the imaging modality comprises an ultrasound transducer.

25. The system of any one of Examples 22-24, further comprising an ablation device, wherein the ablation device comprises an radiofrequency generator.

26. A method of providing a system for treating a fibroid, the method comprising:

providing a system comprising a processor programmed to execute the program instructions to cause the processor to:

receive fibroid data;

generate user interface data for rendering an interactive user interface on an electronic display;

receive treatment data from a treatment device; and update the user interface with treatment data; and instructing a user to input fibroid data.

27. The method of Example 26 further comprising instructing a user to determine a fibroid treatment order.

28. The method of any of Examples 26-27, wherein the interactive user interface includes:

an interactive fibroid map, and a visual representation of a fibroid data record item, the visual representation comprising a marker on the interactive fibroid map at a respective fibroid location associated with the fibroid data item, the visual representation configured to provide information relating to the fibroid data record item.

29. A system comprising:

a non-transitory computer readable storage medium configured to store program instructions;

an imaging modality configured to transmit information; and a processor programmed to execute the program instructions to cause the processor to:

receive the information from the imaging modality; and generate a user interface data for rendering an interactive user interface on an electronic display, the interactive user interface including:

a fibroid map, and a visual representation of a fibroid data record item, the visual representation comprising a marker on the interactive fibroid map at a respective fibroid location associated with the fibroid data item, the visual representation configured to provide knowledge relating to the fibroid data record item.

30. The system of Example 29, wherein the information comprises at least one of a position of the imaging modality, an orientation of the imagining modality, an insertion depth, an insertion angle, a fibroid location, and a fibroid size.

31. The system of any one of Examples 29-30, wherein the imaging modality comprises a sensor configured to determine at least one of a position and an orientation of the imagining modality.

32. The system of Example 31, wherein the information comprises information representative of at least one of position and orientation of the imaging modality.

33. The system of any one of Examples 31-32, wherein the sensor comprises at least one of an optical tracking system, inertial sensors, and visual markers.

34. The system of any one of Examples 31-33, wherein the imaging modality further comprises an alignment marker configured to emit a signal comprising information representative of at least one of position and orientation of the imaging modality.

35. The system of Example 34, further comprising a receiver configured to receive the signal emitted by the alignment marker.

36. The system of any one of Examples 34-35, wherein the alignment marker comprises a source of electromagnetic radiation.

37. The system of any one of Examples 29-36, further comprising an ablation tool.

38. The system of Example 37, wherein the ablation tool is coupled to the imaging modality.

39. The system of any one of Examples 29-38, further comprising a tracking system configured to at least partially determine at least one of position, orientation, and motion of the imaging modality.

40. The system of any one of Examples 29-39, wherein the processor is configured to generate the interactive user interface using the information received from the imaging modality.

41. The system of any one of Examples 29-40, wherein the visual representation is configured to overlay the interactive fibroid map.

IX. Additional Examples

Each of the processes, methods, and algorithms described in the preceding sections may be embodied in, and fully or partially automated by, code modules stored in memory and executed by one or more computer systems or computer processors comprising computer hardware. The processes and algorithms may be implemented partially or wholly in application-specific circuitry.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "comprising" as used herein should be given an inclusive rather than exclusive interpretation. For example, a general purpose computer comprising one or more processors should not be interpreted as excluding other computer components, and may possibly include such components as non-transitory memory, input/output devices, and/or network interfaces, among others. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should be construed in accordance with the appended claims and any equivalents thereof.

What is claimed is:

1. A system comprising:
   a non-transitory computer readable storage medium configured to store program instructions; and
   a processor programmed to execute the program instructions to cause the processor to:
      receive fibroid data from a one or more data sources;
      generate user interface data for rendering an interactive user interface on an electronic display, the interactive user interface including:
         an interactive fibroid map that displays an image of at least one uterine fibroid, and
         a visual representation of a fibroid data record item, the visual representation comprising a marker on the interactive fibroid map at a respective fibroid location associated with the fibroid data record item, the visual representation configured to provide information relating to the fibroid data record item;
      receive treatment data from a treatment device, wherein the treatment data comprises at least one of fibroid treatment order, treatment time, or treatment device information; and
      update the interactive fibroid map with the treatment data.

2. The system of claim 1, wherein the processor is programmed to execute the program instructions to cause the processor to receive the treatment data from a user.

3. The system of claim 1, wherein the processor is programmed to execute the program instructions to cause the processor to update the interactive fibroid map with the treatment data in substantially real-time.

4. The system of claim 1, further comprising an imaging modality.

5. The system of claim 4, wherein the imaging modality comprises an ultrasound transducer.

6. The system of claim 5, wherein the treatment data comprises at least one of ultrasound transducer angle or ultrasound transducer position.

7. The system of claim 1, wherein the treatment device comprises an ablation device.

8. The system of claim 7, wherein the ablation device comprises a radiofrequency generator.

9. The system of claim 7, wherein treatment data comprises at least one of needle deployment depth, electrode deployment length, ablation time, ablation temperature, radiofrequency power, and radiofrequency temperature.

10. The system of claim 1, wherein the program further programmed to execute the program instructions to cause the processor to generate a treatment report.

11. The system of claim 10, wherein the treatment report comprises information regarding treatment parameters.

12. The system of claim 10, wherein the treatment report comprises information regarding at least one of fibroid location, estimated fibroid size, fibroid treated status, number of fibroids, or fibroid treatment order.

13. The system of claim 10, wherein the treatment report is generated in response to a user interacting with a treatment report button.

14. The system of claim 10, wherein the treatment report comprises at least one of the interactive fibroid map or an individual fibroid report.

15. The system of claim 10, wherein the treatment report comprises a fibroid warning flag.

16. The system of claim 1, wherein the program further programmed to execute the program instructions to cause the processor to generate multiple treatment reports.

17. A system comprising:
   a non-transitory computer readable storage medium configured to store program instructions; and
   a processor programmed to execute the program instructions to cause the processor to:
      receive fibroid data from a one or more data sources;
      generate user interface data for rendering an interactive user interface on an electronic display, the interactive user interface including:
         an interactive fibroid map that displays an image of at least one uterine fibroid, and
         a visual representation of a fibroid data record item, the visual representation comprising a marker on the interactive fibroid map at a respective fibroid location associated with the fibroid data record item, the visual representation configured to provide information relating to the fibroid data record item; and
         a real-time image of a treatment site overlaid by or alongside the visual representation of the fibroid data record item;
      receive treatment data from a treatment device; and
      update the interactive fibroid map with the treatment data.

* * * * *